(12) United States Patent
Nohr et al.

(10) Patent No.: US 6,168,654 B1
(45) Date of Patent: *Jan. 2, 2001

(54) COLORANT STABILIZERS

(75) Inventors: Ronald Sinclair Nohr, Alpharetta; John Gavin MacDonald, Decatur, both of GA (US)

(73) Assignee: Kimberly-Clark Worldwide, Inc., Neenah, WI (US)

( * ) Notice: Under 35 U.S.C. 154(b), the term of this patent shall be extended for 0 days.

This patent is subject to a terminal disclaimer.

(21) Appl. No.: 09/286,512

(22) Filed: Apr. 6, 1999

Related U.S. Application Data

(60) Division of application No. 08/903,911, filed on Jul. 31, 1997, now Pat. No. 5,891,229, which is a continuation-in-part of application No. 08/843,410, filed on Apr. 15, 1997, now Pat. No. 5,855,655, which is a continuation-in-part of application No. 08/788,863, filed on Jan. 23, 1997, which is a continuation-in-part of application No. 08/757,222, filed on Nov. 27, 1996, now Pat. No. 5,782,963, which is a continuation-in-part of application No. 08/627,693, filed on Mar. 29, 1996, now abandoned.

(51) Int. Cl.[7] .................................................. C09D 11/02
(52) U.S. Cl. ..................................... 106/31.49; 106/31.78
(58) Field of Search .............................. 106/31.49, 31.78

(56) References Cited

U.S. PATENT DOCUMENTS

| | | |
|---|---|---|
| 28,225 | 11/1860 | Heseltine et al. . |
| 28,789 | 4/1860 | Chang . |
| 575,228 | 1/1897 | von Gallois . |
| 582,853 | 5/1897 | Feer . |
| 893,636 | 7/1908 | Maywald . |
| 1,013,544 | 1/1912 | Fuerth . |
| 1,325,971 | 12/1919 | Akashi . |
| 1,364,406 | 1/1921 | Olsen . |
| 1,436,856 | 11/1922 | Brenizer et al. . |
| 1,744,149 | 1/1930 | Staehlin . |
| 1,803,906 | 5/1931 | Krieger et al. . |
| 1,844,199 | 2/1932 | Bicknell et al. . |
| 1,876,880 | 9/1932 | Drapal . |
| 1,880,572 | 10/1932 | Wendt et al. . |
| 1,880,573 | 10/1932 | Wendt et al. . |
| 1,916,350 | 7/1933 | Wendt et al. . |
| 1,916,779 | 7/1933 | Wendt et al. . |
| 1,955,898 | 4/1934 | Wendt et al. . |
| 1,962,111 | 6/1934 | Bamberger . |
| 2,005,378 | 6/1935 | Kiel . |
| 2,005,511 | 6/1935 | Stoll et al. . |
| 2,049,005 | 7/1936 | Gaspar . |
| 2,054,390 | 9/1936 | Rust et al. . |
| 2,058,489 | 10/1936 | Murch et al. . |
| 2,062,304 | 12/1936 | Gaspar . |
| 2,090,511 | 8/1937 | Crossley et al. . |
| 2,097,119 | 10/1937 | Eggert . |
| 2,106,539 | 1/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,154,996 | 4/1939 | Rawling . |
| 2,159,280 | 5/1939 | Mannes et al. . |
| 2,171,976 | 9/1939 | Erickson . |
| 2,181,800 | 11/1939 | Crossley et al. . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |
| 2,243,630 | 5/1941 | Houk et al. . |
| 2,268,324 | 12/1941 | Polgar . |
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,580,461 | 1/1952 | Pearl . |
| 2,601,669 | 6/1952 | Tullsen . |

(List continued on next page.)

FOREIGN PATENT DOCUMENTS

| | | |
|---|---|---|
| 103085 | 4/1937 | (AU) . |
| 12624/88 | 9/1988 | (AU) . |
| 620075 | 5/1962 | (BE) . |

(List continued on next page.)

OTHER PUBLICATIONS

Kubat et al., "Photophysical properties of metal complexes of meso–tetrakis (40sulphonatophenyl) porphyrin," *J. Photochem. and Photobiol.* 96, 93–97, 1996, no month available.*

Abstract for WO 95/00343—A1, *Textiles: Paper: Cellulose*, p. 7, 1995, no month available.*

Maki, Y. et al., "A novel heterocyclic N–oxide, pyrimido[5, 4–g]pteridinetetrone 5–oxide, with multifunctional photooxidative properties", *Chemical Abstracts*, 122, 925 [No. 122:31350F], 1995, no month available.*

(List continued on next page.)

*Primary Examiner*—Helene Klemanski
(74) *Attorney, Agent, or Firm*—Jones & Askew, LLP

(57) ABSTRACT

The present invention is directed to compositions containing a colorant and at least one porphine. The present invention includes an ink set of one or more inks which have substantially identical light fastness properties. One or more of the inks of the ink set includes a colorant and at least one porphine. The porphine imparts light-stability to the colorant so that the colorant does not fade when exposed to electromagnetic radiation such as sunlight or artificial light. The ink set provides a range of colored inks having similar light-stability.

53 Claims, No Drawings

U.S. PATENT DOCUMENTS

| | | |
|---|---|---|
| 2,612,494 | 9/1952 | von Glahn et al. . |
| 2,612,495 | 9/1952 | von Glahn et al. . |
| 2,628,959 | 2/1953 | von Glahn et al. . |
| 2,647,080 | 7/1953 | Joyce . |
| 2,680,685 | 6/1954 | Ratchford . |
| 2,728,784 | 12/1955 | Tholstrup et al. . |
| 2,732,301 | 1/1956 | Robertson et al. . |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,827,358 | 3/1958 | Kaplan et al. . |
| 2,834,773 | 5/1958 | Scalera et al. . |
| 2,875,045 | 2/1959 | Lurie . |
| 2,892,865 | 6/1959 | Giraldi et al. . |
| 2,897,187 | 7/1959 | Koch . |
| 2,936,241 | 5/1960 | Sharp et al. . |
| 2,940,853 | 6/1960 | Sagura et al. . |
| 2,955,067 | 10/1960 | McBurney et al. . |
| 2,992,129 | 7/1961 | Gauthier . |
| 2,992,198 | 7/1961 | Funahashi . |
| 3,030,208 | 4/1962 | Schellenberg et al. . |
| 3,071,815 | 1/1963 | MacKinnon . |
| 3,075,014 | 1/1963 | Palopoli et al. . |
| 3,076,813 | 2/1963 | Sharp . |
| 3,104,973 | 9/1963 | Sprague et al. . |
| 3,114,634 | 12/1963 | Brown et al. . |
| 3,121,632 | 2/1964 | Sprague et al. . |
| 3,123,647 | 3/1964 | Duennenberger et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiebaden . |
| 3,178,285 | 4/1965 | Anderau et al. . |
| 3,238,163 | 3/1966 | O'Neill . |
| 3,242,215 | 3/1966 | Heitmiller . |
| 3,248,337 | 4/1966 | Zirker et al. . |
| 3,266,973 | 8/1966 | Crowley . |
| 3,282,886 | 11/1966 | Gadecki . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,330,659 | 7/1967 | Wainer . |
| 3,341,492 | 9/1967 | Champ et al. . |
| 3,359,109 | 12/1967 | Harder et al. . |
| 3,361,827 | 1/1968 | Biletch . |
| 3,363,969 | 1/1968 | Brooks . |
| 3,385,700 | 5/1968 | Willems et al. . |
| 3,397,984 | 8/1968 | Williams et al. . |
| 3,415,875 | 12/1968 | Luethi et al. . |
| 3,418,118 | 12/1968 | Thommes et al. . |
| 3,445,234 | 5/1969 | Cescon et al. . |
| 3,453,258 | 7/1969 | Parmerter et al. . |
| 3,453,259 | 7/1969 | Parmerter et al. . |
| 3,464,841 | 9/1969 | Skofronick . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,541,142 | 11/1970 | Cragoe, Jr. . |
| 3,546,161 | 12/1970 | Wolheim . |
| 3,547,646 | 12/1970 | Hori et al. . |
| 3,549,367 | 12/1970 | Chang et al. . |
| 3,553,710 | 1/1971 | Lloyd et al. . |
| 3,563,931 | 2/1971 | Horiguchi . |
| 3,565,753 | 2/1971 | Yurkowitz . |
| 3,574,624 | 4/1971 | Reynolds et al. . |
| 3,579,533 | 5/1971 | Yalman . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,617,335 | 11/1971 | Kumura et al. . |
| 3,619,238 | 11/1971 | Kimura et al. . |
| 3,619,239 | 11/1971 | Osada et al. . |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,652,275 | 3/1972 | Baum et al. . |
| 3,660,542 | 5/1972 | Adachi et al. . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |
| 3,676,690 | 7/1972 | McMillin et al. . |
| 3,678,044 | 7/1972 | Adams . |
| 3,689,565 | 9/1972 | Hoffmann et al. . |
| 3,694,241 | 9/1972 | Guthrie et al. . |
| 3,695,879 | 10/1972 | Laming et al. . |
| 3,697,280 | 10/1972 | Strilko . |
| 3,705,043 | 12/1972 | Zablak . |
| 3,707,371 | 12/1972 | Files . |
| 3,729,313 | 4/1973 | Smith . |
| 3,737,628 | 6/1973 | Azure . |
| 3,765,896 | 10/1973 | Fox . |
| 3,775,130 | 11/1973 | Enomoto et al. . |
| 3,788,849 | 1/1974 | Taguchi et al. . |
| 3,799,773 | 3/1974 | Watarai et al. . |
| 3,800,439 | 4/1974 | Sokolski et al. . |
| 3,801,329 | 4/1974 | Sandner et al. . |
| 3,817,752 | 6/1974 | Laridon et al. . |
| 3,840,338 | 10/1974 | Zviak et al. . |
| 3,844,790 | 10/1974 | Chang et al. . |
| 3,870,524 | 3/1975 | Watanabe et al. . |
| 3,873,500 | 3/1975 | Kato et al. . |
| 3,876,496 | 4/1975 | Lozano . |
| 3,887,450 | 6/1975 | Gilano et al. . |
| 3,895,949 | 7/1975 | Akamatsu . |
| 3,901,779 | 8/1975 | Mani . |
| 3,910,993 | 10/1975 | Avar et al. . |
| 3,914,165 | 10/1975 | Gaske . |
| 3,914,166 | 10/1975 | Rudolph et al. . |
| 3,915,824 | 10/1975 | McGinniss . |
| 3,919,323 | 11/1975 | Houlihan et al. . |
| 3,926,641 | 12/1975 | Rosen . |
| 3,928,264 | 12/1975 | Young, Jr. et al. . |
| 3,933,682 | 1/1976 | Bean . |
| 3,952,129 | 4/1976 | Matsukawa et al. . |
| 3,960,685 | 6/1976 | Sano et al. . |
| 3,965,157 | 6/1976 | Harrison . |
| 3,978,132 | 8/1976 | Houlihan et al. . |
| 3,984,248 | 10/1976 | Sturmer . |
| 3,988,154 | 10/1976 | Sturmer . |
| 4,004,998 | 1/1977 | Rosen . |
| 4,012,256 | 3/1977 | Levinos . |
| 4,017,652 | 4/1977 | Gruber . |
| 4,022,674 | 5/1977 | Rosen . |
| 4,024,324 | 5/1977 | Sparks . |

| | | | | | |
|---|---|---|---|---|---|
| 4,039,332 | 8/1977 | Kokelenberg et al. . | 4,302,606 | 11/1981 | Barabas et al. . |
| 4,043,819 | 8/1977 | Baumann . | 4,306,014 | 12/1981 | Kunikane et al. . |
| 4,048,034 | 9/1977 | Martan . | 4,307,182 | 12/1981 | Dalzell et al. . |
| 4,054,719 | 10/1977 | Cordes, III . | 4,308,400 | 12/1981 | Felder et al. . |
| 4,056,665 | 11/1977 | Tayler et al. . | 4,315,807 | 2/1982 | Felder et al. . |
| 4,058,400 | 11/1977 | Crivello . | 4,318,705 | 3/1982 | Nowak et al. . |
| 4,067,892 | 1/1978 | Thorne et al. . | 4,318,791 | 3/1982 | Felder et al. . |
| 4,071,424 | 1/1978 | Dart et al. . | 4,321,118 | 3/1982 | Felder et al. . |
| 4,073,968 | 2/1978 | Miyamoto et al. . | 4,335,054 | 6/1982 | Blaser et al. . |
| 4,077,769 | 3/1978 | Garcia . | 4,335,055 | 6/1982 | Blaser et al. . |
| 4,079,183 | 3/1978 | Green . | 4,336,323 | 6/1982 | Winslow . |
| 4,085,062 | 4/1978 | Virgilio et al. . | 4,343,891 | 8/1982 | Aasen et al. . |
| 4,090,877 | 5/1978 | Streeper . | 4,345,011 | 8/1982 | Drexhage . |
| 4,100,047 | 7/1978 | McCarty . | 4,347,111 | 8/1982 | Gehlhaus et al. . |
| 4,105,572 | 8/1978 | Gorondy . | 4,349,617 | 9/1982 | Kawashiri et al. . |
| 4,107,733 | 8/1978 | Schickedanz . | 4,350,753 | 9/1982 | Shelnut et al. . |
| 4,110,112 | 8/1978 | Roman et al. . | 4,351,893 | 9/1982 | Anderson . |
| 4,111,699 | 9/1978 | Krueger . | 4,356,255 | 10/1982 | Tachikawa et al. . |
| 4,114,028 | 9/1978 | Baio et al. . | 4,357,468 | 11/1982 | Szejtli et al. . |
| 4,126,412 | 11/1978 | Masson et al. . | 4,359,524 | 11/1982 | Masuda et al. . |
| 4,141,807 | 2/1979 | Via . | 4,362,806 | 12/1982 | Whitmore . |
| 4,144,156 | 3/1979 | Kuesters et al. . | 4,367,072 | 1/1983 | Vogtle et al. . |
| 4,148,658 | 4/1979 | Kondoh et al. . | 4,367,280 | 1/1983 | Kondo et al. . |
| 4,162,162 | 7/1979 | Dueber . | 4,369,283 | 1/1983 | Altschuler . |
| 4,171,977 | 10/1979 | Hasegawa et al. . | 4,370,401 | 1/1983 | Winslow et al. . |
| 4,179,577 | 12/1979 | Green . | 4,372,582 | 2/1983 | Geisler . |
| 4,181,807 | 1/1980 | Green . | 4,373,017 | 2/1983 | Masukawa et al. . |
| 4,190,671 | 2/1980 | Vanstone et al. . | 4,373,020 | 2/1983 | Winslow . |
| 4,197,080 | 4/1980 | Mee . | 4,374,984 | 2/1983 | Eichler et al. . |
| 4,199,420 | 4/1980 | Photis . | 4,376,887 | 3/1983 | Greenaway et al. . |
| 4,229,172 | 10/1980 | Baumann et al. . | 4,383,835 | 5/1983 | Preuss et al. . |
| 4,232,106 | 11/1980 | Iwasaki et al. . | 4,390,616 | 6/1983 | Sato et al. . |
| 4,238,492 | 12/1980 | Majoie . | 4,391,867 | 7/1983 | Derick et al. . |
| 4,239,843 | 12/1980 | Hara et al. . | 4,399,209 | 8/1983 | Sanders et al. . |
| 4,239,850 | 12/1980 | Kita et al. . | 4,400,173 | 8/1983 | Beavan . |
| 4,241,155 | 12/1980 | Hara et al. . | 4,401,470 | 8/1983 | Bridger . |
| 4,242,430 | 12/1980 | Hara et al. . | 4,416,961 | 11/1983 | Drexhage . |
| 4,242,431 | 12/1980 | Hara et al. . | 4,421,559 | 12/1983 | Owatari . |
| 4,245,018 | 1/1981 | Hara et al. . | 4,424,325 | 1/1984 | Tsunoda et al. . |
| 4,245,995 | 1/1981 | Hugl et al. . | 4,425,162 | 1/1984 | Sugiyama . |
| 4,246,330 | 1/1981 | Hara et al. . | 4,425,424 | 1/1984 | Altland et al. . |
| 4,248,949 | 2/1981 | Hara et al. . | 4,426,153 | 1/1984 | Libby et al. . |
| 4,250,096 | 2/1981 | Kvita et al. . | 4,434,035 | 2/1984 | Eichler et al. . |
| 4,251,622 | 2/1981 | Kimoto et al. . | 4,447,521 | 5/1984 | Tiers et al. . |
| 4,254,195 | 3/1981 | Hara et al. . | 4,450,227 | 5/1984 | Holmes et al. . |
| 4,256,493 | 3/1981 | Yokoyama et al. . | 4,460,676 | 7/1984 | Fabel . |
| 4,256,817 | 3/1981 | Hara et al. . | 4,467,112 | 8/1984 | Matsuura et al. . |
| 4,258,123 | 3/1981 | Nagashima et al. . | 4,475,999 | 10/1984 | Via . |
| 4,258,367 | 3/1981 | Mansukhani . | 4,477,681 | 10/1984 | Gehlhaus et al. . |
| 4,259,432 | 3/1981 | Kondoh et al. . | 4,489,334 | 12/1984 | Owatari . |
| 4,262,936 | 4/1981 | Miyamoto . | 4,495,041 | 1/1985 | Goldstein . |
| 4,268,605 | 5/1981 | Hara et al. . | 4,496,447 | 1/1985 | Eichler et al. . |
| 4,268,667 | 5/1981 | Anderson . | 4,500,355 | 2/1985 | Shimada et al. . |
| 4,269,926 | 5/1981 | Hara et al. . | 4,508,570 | 4/1985 | Fugii et al. . |
| 4,270,130 | 5/1981 | Houle et al. . | 4,510,392 | 4/1985 | Litt et al. . |
| 4,271,252 | 6/1981 | Hara et al. . | 4,523,924 | 6/1985 | Lacroix . |
| 4,271,253 | 6/1981 | Hara et al. . | 4,524,122 | 6/1985 | Weber et al. . |
| 4,272,244 | 6/1981 | Schlick . | 4,534,838 | 8/1985 | Lin et al. . |
| 4,276,211 | 6/1981 | Singer et al. . | 4,548,896 | 10/1985 | Sabongi et al. . |
| 4,277,497 | 7/1981 | Fromantin . | 4,555,474 | 11/1985 | Kawamura . |
| 4,279,653 | 7/1981 | Makishima et al. . | 4,557,730 | 12/1985 | Bennett et al. . |
| 4,279,982 | 7/1981 | Iwasaki et al. . | 4,565,769 | 1/1986 | Dueber et al. . |
| 4,279,985 | 7/1981 | Nonogaki et al. . | 4,567,171 | 1/1986 | Mangum . |
| 4,284,485 | 8/1981 | Berner . | 4,571,377 | 2/1986 | McGinniss et al. . |
| 4,288,631 | 9/1981 | Ching . | 4,595,745 | 6/1986 | Nakano et al. . |
| 4,289,844 | 9/1981 | Specht et al. . | 4,604,344 | 8/1986 | Irving et al. . |
| 4,290,870 | 9/1981 | Kondoh et al. . | 4,605,442 | 8/1986 | Kawashita et al. . |
| 4,293,458 | 10/1981 | Gruenberger et al. . | 4,613,334 | 9/1986 | Thomas et al. . |
| 4,298,679 | 11/1981 | Shinozaki et al. . | 4,614,723 | 9/1986 | Schmidt et al. . |
| 4,300,123 | 11/1981 | McMillin et al. . | 4,617,380 | 10/1986 | Hinson et al. . |
| 4,301,223 | 11/1981 | Nakamura et al. . | 4,620,875 | 11/1986 | Shimada et al. . |

| | | |
|---|---|---|
| 4,620,876 | 11/1986 | Fugii et al. . |
| 4,622,286 | 11/1986 | Sheets . |
| 4,631,085 | 12/1986 | Kawanishi et al. . |
| 4,632,891 | 12/1986 | Banks et al. . |
| 4,632,895 | 12/1986 | Patel et al. . |
| 4,634,644 | 1/1987 | Irving et al. . |
| 4,638,340 | 1/1987 | Iiyama et al. . |
| 4,647,310 | 3/1987 | Shimada et al. . |
| 4,655,783 | 4/1987 | Reinert et al. . |
| 4,663,275 | 5/1987 | West et al. . |
| 4,663,641 | 5/1987 | Iiyama et al. . |
| 4,668,533 | 5/1987 | Miller . |
| 4,672,041 | 6/1987 | Jain . |
| 4,698,291 | 10/1987 | Koibuchi et al. . |
| 4,701,402 | 10/1987 | Patel et al. . |
| 4,702,996 | 10/1987 | Griffing et al. . |
| 4,704,133 | 11/1987 | Reinert et al. . |
| 4,707,161 | 11/1987 | Thomas et al. . |
| 4,707,425 | 11/1987 | Sasagawa et al. . |
| 4,707,430 | 11/1987 | Ozawa et al. . |
| 4,711,668 | 12/1987 | Shimada et al. . |
| 4,711,802 | 12/1987 | Tannenbaum . |
| 4,713,113 | 12/1987 | Shimada et al. . |
| 4,720,450 | 1/1988 | Ellis . |
| 4,721,531 | 1/1988 | Wildeman et al. . |
| 4,721,734 | 1/1988 | Gehlhaus et al. . |
| 4,724,021 | 2/1988 | Martin et al. . |
| 4,724,201 | 2/1988 | Okazaki et al. . |
| 4,725,527 | 2/1988 | Robillard . |
| 4,727,824 | 3/1988 | Ducharme et al. . |
| 4,732,615 | 3/1988 | Kawashita et al. . |
| 4,737,190 | 4/1988 | Shimada et al. . |
| 4,737,438 | 4/1988 | Ito et al. . |
| 4,740,451 | 4/1988 | Kohara . |
| 4,745,042 | 5/1988 | Sasago et al. . |
| 4,746,735 | 5/1988 | Kruper, Jr. et al. . |
| 4,752,341 | 6/1988 | Rock . |
| 4,755,450 | 7/1988 | Sanders et al. . |
| 4,761,181 | 8/1988 | Suzuki . |
| 4,766,050 | 8/1988 | Jerry . |
| 4,766,055 | 8/1988 | Kawabata et al. . |
| 4,770,667 | 9/1988 | Evans et al. . |
| 4,772,291 | 9/1988 | Shibanai et al. . |
| 4,772,541 | 9/1988 | Gottschalk . |
| 4,775,386 | 10/1988 | Reinert et al. . |
| 4,786,586 | 11/1988 | Lee et al. . |
| 4,789,382 | 12/1988 | Neumann et al. . |
| 4,790,565 | 12/1988 | Steed . |
| 4,800,149 | 1/1989 | Gottschalk . |
| 4,803,008 | 2/1989 | Ciolino et al. . |
| 4,808,189 | 2/1989 | Oishi et al. . |
| 4,812,139 | 3/1989 | Brodmann . |
| 4,812,517 | 3/1989 | West . |
| 4,813,970 | 3/1989 | Kirjanov et al. . |
| 4,822,714 | 4/1989 | Sanders . |
| 4,831,068 | 5/1989 | Reinert et al. . |
| 4,834,771 | 5/1989 | Yamauchi et al. . |
| 4,837,106 | 6/1989 | Ishikawa et al. . |
| 4,837,331 | 6/1989 | Yamanishi et al. . |
| 4,838,938 | 6/1989 | Tomida et al. . |
| 4,839,269 | 6/1989 | Okazaki et al. . |
| 4,849,320 | 7/1989 | Irving et al. . |
| 4,853,037 | 8/1989 | Johnson et al. . |
| 4,853,398 | 8/1989 | Carr et al. . |
| 4,854,971 | 8/1989 | Gane et al. . |
| 4,857,438 | 8/1989 | Loerzer et al. . |
| 4,861,916 | 8/1989 | Kohler et al. . |
| 4,865,942 | 9/1989 | Gottschalk et al. . |
| 4,874,391 | 10/1989 | Reinert . |
| 4,874,899 | 10/1989 | Hoelderich et al. . |
| 4,885,395 | 12/1989 | Hoelderich . |
| 4,886,774 | 12/1989 | Doi . |
| 4,892,941 | 1/1990 | Dolphin et al. . |
| 4,895,880 | 1/1990 | Gottschalk . |
| 4,900,581 | 2/1990 | Stuke et al. . |
| 4,902,299 | 2/1990 | Anton . |
| 4,902,725 | 2/1990 | Moore . |
| 4,902,787 | 2/1990 | Freeman . |
| 4,911,732 | 3/1990 | Neumann et al. . |
| 4,911,899 | 3/1990 | Hagiwara et al. . |
| 4,917,956 | 4/1990 | Rohrbach . |
| 4,921,317 | 5/1990 | Suzuki et al. . |
| 4,925,770 | 5/1990 | Ichiura et al. . |
| 4,925,777 | 5/1990 | Inoue et al. . |
| 4,926,190 | 5/1990 | Lavar . |
| 4,933,265 | 6/1990 | Inoue et al. . |
| 4,933,948 | 6/1990 | Herkstroeter . |
| 4,937,161 | 6/1990 | Kita et al. . |
| 4,942,113 | 7/1990 | Trundle . |
| 4,950,304 | 8/1990 | Reinert et al. . |
| 4,952,478 | 8/1990 | Miyagawa et al. . |
| 4,952,680 | 8/1990 | Schmeidl . |
| 4,954,380 | 9/1990 | Kanome et al. . |
| 4,954,416 | 9/1990 | Wright et al. . |
| 4,956,254 | 9/1990 | Washizu et al. . |
| 4,964,871 | 10/1990 | Reinert et al. . |
| 4,965,294 | 10/1990 | Ohngemach et al. . |
| 4,966,607 | 10/1990 | Shinoki et al. . |
| 4,966,833 | 10/1990 | Inoue . |
| 4,968,596 | 11/1990 | Inoue et al. . |
| 4,968,813 | 11/1990 | Rule et al. . |
| 4,985,345 | 1/1991 | Hayakawa et al. . |
| 4,987,056 | 1/1991 | Imahashi et al. . |
| 4,988,561 | 1/1991 | Wason . |
| 4,997,745 | 3/1991 | Kawamura et al. . |
| 5,001,330 | 3/1991 | Koch . |
| 5,002,853 | 3/1991 | Aoai et al. . |
| 5,002,993 | 3/1991 | West et al. . |
| 5,003,142 | 3/1991 | Fuller . |
| 5,006,758 | 4/1991 | Gellert et al. . |
| 5,013,959 | 5/1991 | Kogelschatz . |
| 5,017,195 | 5/1991 | Satou et al. . |
| 5,023,129 | 6/1991 | Morganti et al. . |
| 5,025,036 | 6/1991 | Carson et al. . |
| 5,026,425 | 6/1991 | Hindagolla et al. . |
| 5,026,427 | 6/1991 | Mitchell et al. . |
| 5,028,262 | 7/1991 | Barlow, Jr. et al. . |
| 5,028,792 | 7/1991 | Mullis . |
| 5,030,243 | 7/1991 | Reinert . |
| 5,030,248 | 7/1991 | Meszaros . |
| 5,034,526 | 7/1991 | Bonham et al. . |
| 5,037,726 | 8/1991 | Kojima et al. . |
| 5,045,435 | 9/1991 | Adams et al. . |
| 5,045,573 | 9/1991 | Kohler et al. . |
| 5,047,556 | 9/1991 | Kohler et al. . |
| 5,049,777 | 9/1991 | Mechtersheimer . |
| 5,053,320 | 10/1991 | Robbillard . |
| 5,055,579 | 10/1991 | Pawlowski et al. . |
| 5,057,562 | 10/1991 | Reinert . |
| 5,068,364 | 11/1991 | Takagaki et al. . |
| 5,069,681 | 12/1991 | Bouwknegt et al. . |
| 5,070,001 | 12/1991 | Stahlhofen . |
| 5,073,448 | 12/1991 | Vieira et al. . |
| 5,074,885 | 12/1991 | Reinert . |
| 5,076,808 | 12/1991 | Hahn et al. . |
| 5,085,698 | 2/1992 | Ma et al. . |
| 5,087,550 | 2/1992 | Blum et al. . |
| 5,089,050 | 2/1992 | Vieira et al. . |
| 5,089,374 | 2/1992 | Saeva . |
| 5,096,456 | 3/1992 | Reinert et al. . |
| 5,096,489 | 3/1992 | Laver . |
| 5,096,781 | 3/1992 | Vieira et al. . |

| | | | | | |
|---|---|---|---|---|---|
| 5,098,477 | 3/1992 | Vieira et al. | 5,271,765 | 12/1993 | Ma . |
| 5,098,793 | 3/1992 | Rohrbach et al. | 5,272,201 | 12/1993 | Ma et al. |
| 5,098,806 | 3/1992 | Robillard . | 5,275,646 | 1/1994 | Marshall et al. |
| 5,106,723 | 4/1992 | West et al. | 5,279,652 | 1/1994 | Kaufmann et al. |
| 5,108,505 | 4/1992 | Moffat . | 5,282,894 | 2/1994 | Albert et al. |
| 5,108,874 | 4/1992 | Griffing et al. | 5,284,734 | 2/1994 | Blum et al. |
| 5,110,706 | 5/1992 | Yumoto et al. | 5,286,286 | 2/1994 | Winnik et al. |
| 5,110,709 | 5/1992 | Aoai et al. | 5,286,288 | 2/1994 | Tobias et al. |
| 5,114,832 | 5/1992 | Zertani et al. | 5,294,528 | 3/1994 | Furutachi . |
| 5,124,723 | 6/1992 | Laver . | 5,296,275 | 3/1994 | Goman et al. |
| 5,130,227 | 7/1992 | Wade et al. | 5,296,556 | 3/1994 | Frihart . |
| 5,133,803 | 7/1992 | Moffatt . | 5,298,030 | 3/1994 | Burdeska et al. |
| 5,135,940 | 8/1992 | Belander et al. | 5,300,403 | 4/1994 | Angelopolus et al. |
| 5,139,572 | 8/1992 | Kawashima . | 5,300,654 | 4/1994 | Nakajima et al. |
| 5,139,687 | 8/1992 | Borgher, Sr. et al. | 5,302,195 | 4/1994 | Helbrecht . |
| 5,141,556 | 8/1992 | Matrick . | 5,302,197 | 4/1994 | Wickramanayke et al. |
| 5,141,797 | 8/1992 | Wheeler . | 5,310,778 | 5/1994 | Shor et al. |
| 5,144,964 | 9/1992 | Demian . | 5,312,713 | 5/1994 | Yokoyama et al. |
| 5,147,901 | 9/1992 | Rutsch et al. | 5,312,721 | 5/1994 | Gesign . |
| 5,153,104 | 10/1992 | Rossman et al. | 5,324,349 | 6/1994 | Sano et al. |
| 5,153,105 | 10/1992 | Sher et al. | 5,328,504 | 7/1994 | Ohnishi . |
| 5,153,166 | 10/1992 | Jain et al. | 5,330,860 | 7/1994 | Grot et al. |
| 5,160,346 | 11/1992 | Fuso et al. | 5,334,455 | 8/1994 | Noren et al. |
| 5,160,372 | 11/1992 | Matrick . | 5,338,319 | 8/1994 | Kaschig et al. |
| 5,166,041 | 11/1992 | Murofushi et al. | 5,340,631 | 8/1994 | Matsuzawa et al. |
| 5,169,436 | 12/1992 | Matrick . | 5,340,854 | 8/1994 | Martic et al. |
| 5,169,438 | 12/1992 | Matrick . | 5,344,483 | 9/1994 | Hinton . |
| 5,173,112 | 12/1992 | Matrick et al. | 5,356,464 | 10/1994 | Hickman et al. |
| 5,176,984 | 1/1993 | Hipps, Sr. et al. | 5,362,592 | 11/1994 | Murofushi et al. |
| 5,178,420 | 1/1993 | Shelby . | 5,368,689 | 11/1994 | Agnemo . |
| 5,180,425 | 1/1993 | Matrick et al. | 5,372,387 | 12/1994 | Wajda . |
| 5,180,652 | 1/1993 | Yamaguchi et al. | 5,372,917 | 12/1994 | Tsuchida et al. |
| 5,181,935 | 1/1993 | Reinert et al. | 5,374,335 | 12/1994 | Lindgren et al. |
| 5,185,236 | 2/1993 | Shiba et al. | 5,376,503 | 12/1994 | Audett et al. |
| 5,187,045 | 2/1993 | Bonham et al. | 5,383,961 | 1/1995 | Bauer et al. |
| 5,187,049 | 2/1993 | Sher et al. | 5,384,186 | 1/1995 | Trinh . |
| 5,190,565 | 3/1993 | Berenbaum et al. | 5,393,580 | 2/1995 | Ma et al. |
| 5,190,710 | 3/1993 | Kletecka . | 5,401,303 | 3/1995 | Stoffel et al. |
| 5,190,845 | 3/1993 | Hashimoto et al. | 5,401,562 | 3/1995 | Akao . |
| 5,193,854 | 3/1993 | Borowski, Jr. et al. | 5,415,686 | 5/1995 | Kurabayashi et al. |
| 5,196,295 | 3/1993 | Davis . | 5,415,976 | 5/1995 | Ali . |
| 5,197,991 | 3/1993 | Rembold . | 5,424,407 | 6/1995 | Tanaka et al. |
| 5,198,330 | 3/1993 | Martic et al. | 5,425,978 | 6/1995 | Berneth et al. |
| 5,202,209 | 4/1993 | Winnik et al. | 5,426,164 | 6/1995 | Babb et al. |
| 5,202,210 | 4/1993 | Matsuoka et al. | 5,427,415 | 6/1995 | Chang . |
| 5,202,211 | 4/1993 | Vercoulen . | 5,429,628 | 7/1995 | Trinh et al. |
| 5,202,212 | 4/1993 | Shin et al. | 5,431,720 | 7/1995 | Nagai et al. |
| 5,202,213 | 4/1993 | Nakahara et al. | 5,432,274 | 7/1995 | Luong et al. |
| 5,202,215 | 4/1993 | Kanakura et al. | 5,445,651 | 8/1995 | Thoen et al. |
| 5,202,221 | 4/1993 | Imai et al. | 5,445,842 | 8/1995 | Tanaka et al. |
| 5,205,861 | 4/1993 | Matrick . | 5,455,143 | 10/1995 | Ali . |
| 5,208,136 | 5/1993 | Zanoni et al. | 5,459,014 | 10/1995 | Nishijima et al. |
| 5,209,814 | 5/1993 | Felten et al. | 5,464,472 | 11/1995 | Horn et al. |
| 5,219,703 | 6/1993 | Bugner et al. | 5,466,283 | 11/1995 | Kondo et al. |
| 5,221,334 | 6/1993 | Ma et al. | 5,474,691 | 12/1995 | Severns . |
| 5,224,197 | 6/1993 | Zanoni et al. | 5,475,080 | 12/1995 | Gruber et al. |
| 5,224,476 | 7/1993 | Schultz et al. | 5,476,540 | 12/1995 | Shields et al. |
| 5,224,987 | 7/1993 | Matrick . | 5,479,949 | 1/1996 | Battard et al. |
| 5,226,957 | 7/1993 | Wickramanayake et al. | 5,489,503 | 2/1996 | Toan . |
| 5,227,022 | 7/1993 | Leonhardt et al. | 5,498,345 | 3/1996 | Jollenbeck et al. |
| 5,241,059 | 8/1993 | Yoshinaga . | 5,501,774 | 3/1996 | Burke . |
| 5,244,476 | 9/1993 | Schulz et al. | 5,503,664 | 4/1996 | Sano et al. |
| 5,250,109 | 10/1993 | Chan et al. | 5,509,957 | 4/1996 | Toan et al. |
| 5,254,429 | 10/1993 | Gracia et al. | 5,531,821 | 7/1996 | Wu . |
| 5,256,193 | 10/1993 | Winnik et al. | 5,532,112 | 7/1996 | Kohler et al. |
| 5,258,274 | 11/1993 | Helland et al. | 5,541,633 | 7/1996 | Winnik et al. |
| 5,261,953 | 11/1993 | Vieira et al. | 5,543,459 | 8/1996 | Hartmann et al. |
| 5,262,276 | 11/1993 | Kawamura . | 5,571,313 | 11/1996 | Mafune et al. |
| 5,268,027 | 12/1993 | Chan et al. | 5,575,891 | 11/1996 | Trokhan et al. |
| 5,270,078 | 12/1993 | Walker et al. | 5,580,369 | 12/1996 | Belding et al. |
| 5,271,764 | 12/1993 | Winnik et al. | 5,607,803 | 3/1997 | Murofushi et al. |

| | | | | | | |
|---|---|---|---|---|---|---|
| 5,782,963 | * | 7/1998 | Nohr et al. ......... 106/31.49 | 0629664 | 2/1995 | (EP) . |
| 5,855,655 | * | 1/1999 | Nohr et al. ......... 106/31.49 | 2245010 | 4/1975 | (FR) . |
| 5,891,229 | * | 4/1999 | Nohr et al. ......... 106/31.49 | 2383157 | 10/1978 | (FR) . |

FOREIGN PATENT DOCUMENTS

| | | | | | |
|---|---|---|---|---|---|
| 637169 | 3/1964 | (BE) . | 275245 | 10/1928 | (GB) . |
| 413257 | 10/1932 | (CA) . | 349339 | 5/1931 | (GB) . |
| 458808 | 12/1936 | (CA) . | 355686 | 8/1931 | (GB) . |
| 460268 | 10/1949 | (CA) . | 399753 | 10/1933 | (GB) . |
| 461082 | 11/1949 | (CA) . | 441085 | 1/1936 | (GB) . |
| 463021 | 2/1950 | (CA) . | 463515 | 4/1937 | (GB) . |
| 463022 | 2/1950 | (CA) . | 492711 | 9/1938 | (GB) . |
| 465495 | 5/1950 | (CA) . | 518612 | 3/1940 | (GB) . |
| 465496 | 5/1950 | (CA) . | 539912 | 9/1941 | (GB) . |
| 465499 | 5/1950 | (CA) . | 626727 | 7/1947 | (GB) . |
| 483214 | 5/1952 | (CA) . | 600451 | 4/1948 | (GB) . |
| 517364 | 10/1955 | (CA) . | 616362 | 1/1949 | (GB) . |
| 537687 | 3/1957 | (CA) . | 618616 | 2/1949 | (GB) . |
| 552565 | 2/1958 | (CA) . | 779389 | 7/1957 | (GB) . |
| 571792 | 3/1959 | (CA) . | 1372884 | 11/1974 | (GB) . |
| 779239 | 2/1968 | (CA) . | 2146357 | 4/1985 | (GB) . |
| 930103 | 7/1973 | (CA) . | 662500 | 4/1964 | (IT) . |
| 2053094 | 4/1992 | (CA) . | 43-15663 | 7/1968 | (JP) . |
| 603767 | 8/1978 | (CH) . | 47-26653 | 7/1972 | (JP) . |
| 197808 | 5/1988 | (CH) . | 47-45409 | 11/1972 | (JP) . |
| 94118 | 5/1958 | (CZ) . | 49-8909 | 2/1974 | (JP) . |
| 1047787 | 12/1957 | (DE) . | 50-65592 | 6/1975 | (JP) . |
| 1022801 | 1/1958 | (DE) . | 51-17802 | 2/1976 | (JP) . |
| 1039835 | 9/1958 | (DE) . | 53-104321 | 9/1978 | (JP) . |
| 1040562 | 10/1958 | (DE) . | 55-62059 | 5/1980 | (JP) . |
| 1045414 | 12/1958 | (DE) . | 55-90506 | 7/1980 | (JP) . |
| 1047013 | 12/1958 | (DE) . | 0014233 | 2/1981 | (JP) . |
| 1132540 | 7/1962 | (DE) . | 56-14569 | 2/1981 | (JP) . |
| 1154069 | 9/1963 | (DE) . | 56-24472 | 3/1981 | (JP) . |
| 1240811 | 5/1967 | (DE) . | 56-36556 | 4/1981 | (JP) . |
| 2202497 | 8/1972 | (DE) . | 57-61055 | 4/1982 | (JP) . |
| 2432563 | 2/1975 | (DE) . | 57-128283 | 8/1982 | (JP) . |
| 2437380 | 2/1975 | (DE) . | 57-171775 | 10/1982 | (JP) . |
| 2444520 | 3/1975 | (DE) . | 58-124452 | 7/1983 | (JP) . |
| 2416259 | 10/1975 | (DE) . | 58-125770 | 7/1983 | (JP) . |
| 2714978 | 10/1977 | (DE) . | 58-222164 | 12/1983 | (JP) . |
| 2722264 | 11/1978 | (DE) . | 59-89360 | 5/1984 | (JP) . |
| 158237 | 1/1983 | (DE) . | 29219270 | 12/1984 | (JP) . |
| 3126433 | 1/1983 | (DE) . | 59-219270 | 4/1985 | (JP) . |
| 3415033 | 10/1984 | (DE) . | 60-192729 | 10/1985 | (JP) . |
| 281512 | 9/1989 | (DE) . | 60-239739 | 11/1985 | (JP) . |
| 3921600 | 1/1990 | (DE) . | 60-239740 | 11/1985 | (JP) . |
| 3833437 | 4/1990 | (DE) . | 60-239741 | 11/1985 | (JP) . |
| 3833438 | 4/1990 | (DE) . | 60-239743 | 11/1985 | (JP) . |
| 004036328 | 7/1991 | (DE) . | 61-14994 | 1/1986 | (JP) . |
| 4132288 | 4/1992 | (DE) . | 61-14995 | 1/1986 | (JP) . |
| 4126461 | 2/1993 | (DE) . | 61-21184 | 1/1986 | (JP) . |
| 0003884 | 9/1979 | (EP) . | 61-288 | 1/1986 | (JP) . |
| 0029284 | 5/1981 | (EP) . | 61-3781 | 1/1986 | (JP) . |
| 0127574 | 12/1984 | (EP) . | 61-25885 | 2/1986 | (JP) . |
| 0223587 | 5/1987 | (EP) . | 61-30592 | 2/1986 | (JP) . |
| 0262533 | 4/1988 | (EP) . | 61-40366 | 2/1986 | (JP) . |
| 0280458 | 8/1988 | (EP) . | 61-128973 | 6/1986 | (JP) . |
| 0308274 | 3/1989 | (EP) . | 61-97025 | 9/1986 | (JP) . |
| 0351615 | 1/1990 | (EP) . | 61-222789 | 10/1986 | (JP) . |
| 0371304 | 6/1990 | (EP) . | 61-247703 | 11/1986 | (JP) . |
| 0373662 | 6/1990 | (EP) . | 61-285403 | 12/1986 | (JP) . |
| 0375160 | 6/1990 | (EP) . | 62-7703 | 1/1987 | (JP) . |
| 0390439 | 10/1990 | (EP) . | 62-100557 | 5/1987 | (JP) . |
| 0458140A1 | 10/1991 | (EP) . | 62-97881 | 5/1987 | (JP) . |
| 0458140 | 11/1991 | (EP) . | 62-127281 | 6/1987 | (JP) . |
| 0468465 | 1/1992 | (EP) . | 424756 | 1/1988 | (JP) . |
| 0542286 | 5/1993 | (EP) . | 63-43959 | 2/1988 | (JP) . |
| 000571190 | 11/1993 | (EP) . | 63-48370 | 3/1988 | (JP) . |
| 0608433 | 8/1994 | (EP) . | 63-95439 | 4/1988 | (JP) . |
| 0609159 | 8/1994 | (EP) . | 63-95440 | 4/1988 | (JP) . |
| | | | 63-95445 | 4/1988 | (JP) . |
| | | | 63-95446 | 4/1988 | (JP) . |

| | | |
|---|---|---|
| 63-95447 | 4/1988 | (JP) . |
| 63-95448 | 4/1988 | (JP) . |
| 63-95449 | 4/1988 | (JP) . |
| 63-95450 | 4/1988 | (JP) . |
| 63-151946 | 6/1988 | (JP) . |
| 63-164953 | 7/1988 | (JP) . |
| 63-165498 | 7/1988 | (JP) . |
| 63-223077 | 9/1988 | (JP) . |
| 63-223078 | 9/1988 | (JP) . |
| 63-243101 | 10/1988 | (JP) . |
| 63-199781 | 12/1988 | (JP) . |
| 64-15049 | 1/1989 | (JP) . |
| 64-29337 | 1/1989 | (JP) . |
| 64-40948 | 2/1989 | (JP) . |
| 64-014948 | 3/1989 | (JP) . |
| 1-128063 | 5/1989 | (JP) . |
| 1146974 | 6/1989 | (JP) . |
| 01210477 | 8/1989 | (JP) . |
| 1288854 | 11/1989 | (JP) . |
| 2-58573 | 2/1990 | (JP) . |
| 292957 | 4/1990 | (JP) . |
| 2179642 | 7/1990 | (JP) . |
| 2282261 | 11/1990 | (JP) . |
| 3-134072 | 6/1991 | (JP) . |
| 03163566 | 7/1991 | (JP) . |
| 3-170415 | 7/1991 | (JP) . |
| 3-206439 | 9/1991 | (JP) . |
| 3-203694 | 12/1991 | (JP) . |
| 3284668 | 12/1991 | (JP) . |
| 4023884 | 1/1992 | (JP) . |
| 4023885 | 1/1992 | (JP) . |
| 4-45174 | 2/1992 | (JP) . |
| 4100801 | 4/1992 | (JP) . |
| 4-136075 | 5/1992 | (JP) . |
| 04356087 | 12/1992 | (JP) . |
| 543806 | 2/1993 | (JP) . |
| 561220 | 3/1993 | (JP) . |
| 5080506 | 4/1993 | (JP) . |
| 05119506 | 5/1993 | (JP) . |
| 5134447 | 5/1993 | (JP) . |
| 5-140498 | 6/1993 | (JP) . |
| 2-219869 | 9/1993 | (JP) . |
| 5263067 | 10/1993 | (JP) . |
| 680915 | 3/1994 | (JP) . |
| 6116555 | 4/1994 | (JP) . |
| 6116556 | 4/1994 | (JP) . |
| 6116557 | 4/1994 | (JP) . |
| 6-175584 | 6/1994 | (JP) . |
| 6214339 | 8/1994 | (JP) . |
| 6256494 | 9/1994 | (JP) . |
| 6256633 | 9/1994 | (JP) . |
| 7113828 | 4/1972 | (NL) . |
| 1310767 | 5/1987 | (RU) . |
| 1772118 | 10/1992 | (SU) . |
| 92/11295 | 7/1992 | (WO) . |
| 93/06597 | 4/1993 | (WO) . |
| 94/01503 | 1/1994 | (WO) . |
| 94/22500 | 10/1994 | (WO) . |
| 94/22501 | 10/1994 | (WO) . |
| 95/04955 | 2/1995 | (WO) . |
| 96/00740 | 1/1996 | (WO) . |
| 96/19502 | 6/1996 | (WO) . |
| 96/22335 | 7/1996 | (WO) . |

OTHER PUBLICATIONS

Abstract of patent, JP 6–80915 (Canon Inc.), Mar. 22, 1994. 1994.*

Abstract of patent, JP 06–43573 (Iku Meji) (Feb. 18, 1994). 1994.*

Pitchumani, K. et al., "Modification of chemical reactivity upon cyclodextrin encapsulation", *Chemical Abstracts*, 121, 982 [No. 121:133624v], 1994, no month available.*

Derwent Publications Ltd., London, JP 05297627 (Fujitsu Ltd.), Nov. 12, 1993. (Abstract). 1993.*

Patent Abstracts of Japan, JP 5241369 (Bando Chem Ind Ltd et al.), Sep. 21, 1993. (Abstract). 1993.*

Derwent Publications Ltd., London, JP 05232738 (Yamazaki, T.), Sep. 10, 1993. (Abstract). 1993.*

Derwent Publications Ltd., London, EP 000559310 (Zeneca Ltd.), Sep. 8, 1993. (Abstract). 1993.*

Derwent Publications Ltd., London, J,A, 5–230410 (Seiko Epson Corp), Sep. 7, 1993. (Abstract). 1993.*

Derwent Publications Ltd., London, JP 5–230407 (Mitsubishi Kasei Corp), Sep. 7, 1993. (Abstract). 1993.*

Abstract Of Patent, JP 405230410 (Seiko Epson Corp.), Sep. 7, 1993. (Abstract) . 1993.*

Abstract Of Patent, JP 405230407 (Mitsubishi Kasei Corp.), Sep. 7, 1993. (Abstract). 1993.*

Patent Abstracts of Japan, JP 5197198 (Bando Chem Ind Ltd et al.), Aug. 6, 1993. (Abstract) . 1993.*

Database WPI—Derwent Publications Ltd., London, J,A, 5197069 (Bando Chem), Aug. 6, 1993. (Abstract) . 1993.*

Abstract of patent, JP 5–195450 (Nitto Boseki Co. Ltd), Aug. 3, 1993. 1993.*

Patent Abstracts of Japan, JP 5181308 (Bando Chem Ind Ltd et al.), Jul. 23, 1993. (Abstract). 1993.*

Patent Abstracts of Japan, JP 5181310 (Bando Chem Ind Ltd et al.), Jul. 23, 1993. (Abstract). 1993.*

Derwent Publications Ltd., London, JP 5–132638 (Mitsubishi Kasei Corp), May 28, 1993. (Abstract). 1993.*

Abstract Of Patent, JP 405132638 (Mitsubishi Kasei Corp.), May 28, 1993. (Abstract). 1993.*

Derwent Publications Ltd., London, JP 5–125318 (Mitsubishi Kasei Corp), May 21, 1993. (Abstract). 1993.*

Abstract Of Patent, JP 405125318 (Mitsubishi Kasei Corp.), May 21, 1993. (Abstract). 1993.*

Abstract of patent, JP 05–117200 (Hidefumi Hirai et al.) (May 14, 1993). 1993.*

Derwent World Patents Index, JP 5117105 (Mitsui Toatsu Chem Inc.) May 14, 1993. 1993.*

Derwent Publications Ltd., London, JP 05061246 (Ricoh KK), Mar. 12, 1993. (Abstract). 1993.*

Husain, N. et al., "Cyclodextrins as mobile–phase additives in reversed–phase HPLC", *American Laboratory*, 82, 80–87, 1993, no month available.*

Hamilton, D.P., "Tired of Shredding? New Ricoh Method Tries Different Tack", *Wall Street Journal*, B2, 1993, no month available.*

"Cyclodextrins: A Breakthrough for Molecular Encapsulation", *American Maize Products Co. (AMAIZO)*, 1993, no month available.*

Duxbury, "The Photochemistry and Photophysics of Triphenylmethane Dyes in Solid Liquid Media", *Chemical Review*, 93, 381–433, 1993, no month available.*

Abstract of patent, JP 04–351603 (Dec. 7, 1992). 1992.*

Abstract of patent, JP 04–351602, 1992, no month available.*

Derwent Publications Ltd., London, JP 404314769 (Citizen Watch Co. Ltd.), Nov. 5, 1992. (Abstract). 1992.*

Abstract of patent, JP 04315739, 1992, no month available.*

Derwent Publications Ltd., London, JP 04300395 (Funai Denki KK), Oct. 23, 1992. (Abstract). 1992.*

Derwent Publications Ltd., London, JP 404213374 (Mitsubishi Kasei Corp), Aug. 4, 1992. (Abstract). 1992.*
Abstract of patent, JP 04–210228, 1992, no month available.*
Abstract Of Patent, JP 404202571 (Canon Inc.), Jul. 23, 1992. (Abstract). 1992.*
Abstract Of Patent, JP 404202271 (Mitsubishi Kasei Corp.), Jul. 23, 1992. (Abstract). 1992.*
Derwent Publications Ltd., London, JP 4–189877 (Seiko Epson Corp), Jul. 8, 1992. (Abstract). 1992.*
Derwent Publications Ltd., London, JP 404189876 (Seiko Epson Corp), Jul. 8, 1992. (Abstract). 1992.*
Abstract Of Patent, JP 404189877 (Seiko Epson Corp.), Jul. 8, 1992. (Abstract). 1992.*
Derwent Publications Ltd., London, J,A, 4–170479 (Seiko Epson Corp), Jun. 18, 1992. (Abstract). 1992.*
Abstract of patent, JP 04–81402, 1992, no month available.*
Abstract of patent, JP 04–81401, 1992, no month available.*
Kogelschatz, "Silent–discharge driven excimer UV sources and their applications", *Applied Surface Science*, 410–423, 1992, no month available.*
Derwent Publications, Ltd., London, JP 403269167 (Japan Wool Textile KK), Nov. 29, 1991 (Abstract). 1991.*
Derwent Publications Ltd., London, JO 3247676 (Canon KK), Nov. 5, 1991 (Abstract). 1991.*
Abstract of patent, JP 03–220384, 1991, no month available.*
Patent Abstracts of Japan, JP 03184896 (Dainippon Printing Co Ltd.) Aug. 12, 1991. 1991.*
Derwent Publications Ltd., London, JP 3167270 (Mitsubishi Kasei Corp), Jul. 19, 1991. (Abstract). 1991.*
Derwent Publications Ltd., London, JO 3167270 (Mitsubishi Kasei Corp.), Jul. 19, 1991 (Abstract). 1991.*
Derwent Publications Ltd., London, JO 3093870 (Dainippon Ink Chem KK.), Apr. 18, 1991 (Abstract). 1991.*
Abstract of patent, JP 06369890, 1991, no month available.*
Kogelschatz, U. et al., "New Excimer UV Sources for Industrial Applications", *ABB Review*, 391, 1–10, 1991, no month available.*
Abstract of patent, JP 03–41165, 1991, no month available.*
"Coloring/Decoloring Agent for Tonor Use Developed", *Japan Chemical Week*, 1991, no month available.*
Braithwaite, M., et al., "Formulation", *Chemistry & Technology of UV & EB Formulation for Coatings, Inks & Paints*, IV, 11–12, 1991, no month available.*
*Scientific Polymer Products, Inc. Brochure*, 24–31, 1991, no month available.*
Dietliker, K., "Photoiniators for Free Radical and Catioinc Polymerisation", *Chem & Tech of UV & EB Formulation for Coatings, Inks & Paints*, III, 61, 63, 229–232, 280, 405, 1991, no month available.*
Esrom et al., "Large area Photochemical Dry Etching of polymers iwth Incoherent Excimer UV Radiation", *MRS Materials Research Society*, 1–7, 1991, no month available.*
Esrom et al., Excimer Laser–Induced Decompostion of Aluminum Nitride, *Materials Research Society Fall Meeting*, 1–6, 1991, no month available.*
Esrom et al., "Metal deposition with a windowless VUV excimer source", *Applied Surface Science*, 1–5, 1991, no month available.*
Esrom, "Excimer Laser–Induced Surface Activation of Aln for Electroless Metal Deposition", *Mat. Res. Sco.lSymp. Proc.*, 204, 457–465, 1991, no month available.*

Zhang et al., "UV–induced decompositin of adsorbed Cu–acetylacetonate films at room temperature for electroless metal plating", *Applied Surface Science*, 1–6, 1991, no month available.*
"German company develops reuseable paper", *Pulp & Paper*, 1991, no month available.*
Abstract of patent, JP 02289652, 1990, no month available.*
Ohashi et al., "Molecular Mechanics Studies on Inclusion Compounds of Cyanine Dye Monomers and Dimers in Cyclodextrin Cavities," *J. Am. Chem. Soc.*, 112, 5824–5830, 1990, no month available.*
Kogelschatz et al., "New Incoherent Ultraviolet Excimer Sources for Photolytic Material Deposition," *Laser Und Optoelektronik*, 1990, no month available.*
Patent Abstracts of Japan, JP 02141287 (Dainippon Printing Co Ltd.) May 30, 1990. 1990.*
Abstract of Patent, JP 0297957, (Fuji Xerox Co., Ltd.), 1990, no month available.*
Derwent Publications Ltd., London, JP 2091166 (Canon KK), Mar. 30, 1990. (Abstract) . 1990.*
Esrom et al., "Metal Deposition with Incoherent Excimer Radiation", *Mat. Res. Soc. Symp. Proc.*, 158, 189–198, 1990, no month available.*
Esrom, "UV Excimer Laser–Induced Deposition of Palladium from palladiym Acetate Films", *Mat. Res. Soc. Symp. Proc.*, 158, 109–117, 1990, no month available.*
Kogelschatz, U., "Silent Discharges for the Generation of ultraviolet and vacuum ultraviolet excimer radiation", *Pure & Applied Chem.*, 62, 1667–74, 1990, no month available.*
Esrom et al., "Investigation of the mechanism of the UV–induced palladium depostions processf from thin solid palladium acetate films", *Applied Surface Science*, 46, 158–162, 1990, no month available.*
Zhang et al., "VUV synchrotron radiation processing of thin palladium acetate spin–on films for metallic surface patterning", *Applied Surface Science*, 46, 153–157, 1990, no month available.*
Brennan et al., "Stereoelectric effects in ring closure reactions: the 2'-hydroxychalcone—flavanone equilibrium, and related systems,", *Canadian J. Chem.*, 68 (10), pp. 1780–1785, 1990, no month available.*
Abstract of patent, JP 01–299083, 1989, no month available.*
Derwent Publications Ltd., London, J,O, 1182379 (Canon KK), Jul. 20, 1989. (Abstract). 1989.*
Derwent Publications Ltd., London, JO 1011171 (Mitsubishi Chem Ind. KK.), Jan. 13, 1989 (Abstract). 1989.*
Gruber, R.J., et al., "Xerographic Materials", *Encyclopedia of Polymer Science and Engineering*, 17, 918–943, 1989, no month available.*
Pappas, S.P., "Photocrosslinking", *Comph. Pol. Sci.*, 6, 135–148, 1989, no month available.*
Pappas, S.P., "Photoinitiated Polymerization", *Comph. Pol. Sci.*, 4, 337–355, 1989, no month available.*
Kirilenko, G.V. et al., "An analog of the vesicular process with amplitude modulation of the incident light beam", *Chemical Abstracts*, 111, 569 [No. 111:123633b], 1989, no month available.*
Esrom et al., "UV excimer laser–induced pre–nucleation of surfaces followed by electroless metallization", *Chemtronics*, 4, 216–223, 1989, no month available.*
Esrom et al., "VUV light–induced depostion of palladium using an incoherent Xe2* excimer source", *Chemtronics*, 4, 1989, no month available.*

Esrom et al., "UV Light–Induced Depostion of Copper Films", C5–719–C5–725, 1989, no month available.*
Falbe et al., *Rompp Chemie Lexikon*, 9, 270, 1989, no month available.*
Derwent Publications, Ltd., London, SU 1423656 (Kherson Ind Inst), Sep. 15, 1988 (Abstract). 1988.*
Derwent Publications, Ltd., London, EP 0280653 (Ciba Geigy AG), Aug. 31, 1988 (Abstract). 1988.*
Abstract of patent, JP 63–190815, 1988, no month available.*
Patent Abstracts of Japan, JP 63179985 (Tomoegawa Paper Co. Ltd.), Jul. 23, 1988. 1988.*
Derwent World Patents Index, JP 63179977 (Tomoegawa Paper Mfg Co Ltd), Jul. 23, 1988. 1988.*
Furcone, S.Y. et al., "Spin–on B14Sr3Ca3Cu4O16+x superconducting thin films from citrate precursors," *Appl. Phys. Lett.*, 52(25), 2180–2182, 1988, no month available.*
Abstract of patent, JP 63–144329, 1988, no month available.*
Abstract of patent, JP 63–130164, 1988, no month available.*
Derwent Publications, Ltd., London, J6 3112770 (Toray Ind Inc), May 17, 1988 (Abstract). 1988.*
Derwent Publications, Ltd., London, J6 3108074 (Konishiroku Photo KK), May 12, 1988 (Abstract). 1988.*
Derwent Publications, Ltd., London, J6 3108073 (Konishiroku Photo KK), May 12, 1988 (Abstract). 1988.*
Abstract of patent, JP 61–77846, 1988, no month available.*
Abstract of patent, JP 63–73241, 1988, no month available.*
Abstract of patent, JP 63–47762, 1988, no month available.*
Abstract of patent, JP 63–47763, 1988, no month available.*
Abstract of patent, JP 63–47764, 1988, no month available.*
Abstract of patent, JP 63–47765, 1988, no month available.*
Eliasson, B., et al., "UV Excimer Radiation from Dielectric–Barrier Discharges", *Applied Physics B*, 46, 299–303, 1988, no month available.*
Eliasson et al., "New Trends in High Intensity UV Generation", *EPA Newsletter*, (32), 29–40, 1988, no month available.*
Cotton, F.A., "Oxygen: Group Via(16)", *Advanced Inorganic Chemistry*, 5th ed., 473–474, 1988, no month available.*
Derwent Publications, Ltd., London, J6 2270665 (Konishiroku Photo KK), Nov. 25, 1987 (Abstract). 1987.*
Abstract of patent, JP 62–215261, 1987, no month available.*
Database WPI, Derwent Publications Ltd., London, JP 62032082 (Mitsubishi Denki KK), Feb. 12, 1987. (Abstract). 1987.*
Abstract of patent, JP 62–32082, 1987, no month available.*
Derwent Publications Ltd., London, J6 2007772 (Alps Electric KK.), Jan. 14, 1987 (Abstract). 1987.*
Gross et al., "Laser direct–write metallization in thin palladium acetate films", *J. App. Phys.*, 61(4), 1628–1632, 1987, no month available.*
Al–Ismail et al., "Some experimental results on thin polypropylene films loaded with finely–dispersed copper", *Journal of Materials Science*, 415–418, 1987, no month available.*
Baufay et al., "Optical self–regulation during laser–induced oxidation of copper", *J. Appl. Phys*, 61(9), 4640–4651, 1987, no month available.*
Derwent Publications Ltd., London, JA 0284478 (Sanyo Chem Ind Ltd.), Dec. 15, 1986 (Abstract). 1986.*
Abstract of patent, JP 61251842, 1986, no month available.*
Database WPI, Derwent Publications Ltd., London, GB; SU, A, 1098210 (Kutulya L A) Jun. 23, 1986. 1986.*
Abstract of patent, JP 61–97025, 1986, no month available.*
Abstract of patent, JP 61–87760, 1986, no month available.*
Derwent Publications Ltd., London, DL 0234731 (Karl Marx Univ. Leipzig), Apr. 9, 1986. (Abstract). 1986.*
Derwent World Patents Index, SU 1219612 (AS USSR NON–AQ SOLN) Mar. 23, 1986. 1986.*
Derwent Publications, Ltd., London, J6 1041381 (Osaka Prefecture), Feb. 27, 1986 (Abstract). 1986.*
Dialog, JAPIO, JP 61–034057 (Ciba Geigy AG) Feb. 18, 1986. 1986.*
Derwent World Patents Index, JP 61027288 (summitomo Chem Ind KK) Feb. 6, 1986. 1986.*
Sakai et al., "A Novel and Practical Synthetic Method of 3(2H–Furanone Derivatives,"*J. Heterocyclie Chem.*, 23, pp. 1199–1201, 1986, no month available.*
Jellinek, H.H.G. et al., "Evolution of H2O and CO2 During the Copper–Catalyzed Oxidation of Isotactic Polypropylene," *J. Polymer Sci.*, 24, 389–403, 1986, no month available.*
Jellinek, H.H.G. et al., "Diffusion of Ca2+ Catalysts from Cu–Metal Polymer or Cu–Oxide/Polymer Interfaces into Isotactic Polypropylene," *J. Polymer Sci.*, 24, 503–510, 1986, no month available.*
John J. Eisch and Ramiro Sanchez, "Selective, Oxophilic Imination of Ketones with Bis (dichloroaluminum) Phenylimide", *J. Org. Chem.*, 51 (10), 1848–1852, 1986, no month available.*
Derwent Publications Ltd., London, J6 0226575 (Sumitomo Chem Ind Ltd.), Oct. 11, 1985 (Abstract). 1985.*
Abstract of patent, JP 60–156761, 1985, no month available.*
Derwent Publications Ltd., London, J,A, 0011451 (Fugi Photo Film KK), Jan. 21, 1985. (Abstract). 1985.*
Derwent Publications, Ltd., London J6 0011449–A (Taoka Chemical KK) Jan. 21, 1985 (abstract). 1985.*
Roos, G. et al., "Textile applications of photocrosslinkable polymers", *Chemical Abstracts*, 103, 57 [No. 103:23690j], 1985, no month available.*
Derwent World Patents Index, EP 127574 (Ciba Geigy AG), Dec. 5, 1984. 1984.*
Derwent Publications Ltd., London, JP 0198187 (Canon KK), Nov. 9, 1984. (Abstract). 1984.*
Derwent Publications Ltd., London, J,A, 0169883 (Ricoh KK), Sep. 25, 1984. (Abstract). 1984.*
Derwent Publications Ltd., London, JA 0169883 (Ricoh KK), Sep. 25, 1984 (Abstract). 1984.*
Derwent Publications Ltd., London, JA 0198187 (Canon KK), Nov. 9, 1984 (Abstract). 1984.*
Derwent Publications Ltd., London, J,A, 0053563 (Dainippon Toryo KK), Mar. 28, 1984. (Abstract). 1984.*
Derwent Publications Ltd., London, J,A, 0053562 (Dainippon Toryo KK), Mar. 28, 1984. (Abstract). 1984.*
Abstract of Patent, JA 0053563 (Dainippon Toryo KK), Mar. 28, 1984 (Abstract). 1984.*
Abstract of Patent, JA 0053562 (Dainippon Toryo KK), Mar. 28, 1984 Abstract). 1984.*
Derwent Publications Ltd., London, J,A, 0051961 (Dainippon Toryo KK), Mar. 26, 1984). (Abstract). 1984.*
Abstract of Patent, JA 0051961 (Dainippon Toryo KK), Mar. 26, 1984 (Abstract). 1984.*

Saenger, W., "Structural Aspects of Cyclodextrins and Their Inclusion Complexes", *Inclusion Compounds—Structural Aspects of Inclusion Compounds formed by Organic Host*, 2, 231–259, 1984, no month available.*

Szejtli, "Industrial Applications of Cyclodextrins", *Inclusion Compounds: Physical Prop. & Applns*, 3, 331–390, 1984, no month available.*

Kano et al., "Three–Component Complexes of Cyclodextrins. Exciplex Formation in Cyclodextrin Cavity," *J. Inclusion Phenomena* 2, pp. 737–746, 1984, no month available.*

Suzuki et al., "Spectroscopic Investigation of Cyclodextrin Monomers, Derivatives, Polymers and Azo Dyes," *J. Inclusion Phenomena* 2, pp. 715–724, 1984, no month available.*

Abstract of Patent, JA 0222164 (Ricoh KK), Dec. 23, 1983, (Abstract). 1983.*

Abstract of patent, JP 58211426 (Sekisui Plastics KK), (Dec. 8, 1983). 1983.*

Derwent Publications, Ltd., London, EP 0072775 (Ciba Geigy AG), Feb. 23, 1983 (Abstract). 1983.* van Beek, H.C.A, "Light–Induced Colour Changes in Dyes and Materials", *Color Res. and Appl.*, 8, 176–181, 1983, no month available.*

Connors, K.A., "Application of a stoichiometric model of cyclodextrin complex formation", *Chemical Abstracts*, 98, 598 [No. 98:53067g], 1983, no month available.*

Abstract of Patent, EP 0065617 (IBM Corp.), Dec. 1, 1982 (Abstract). 1982.*

Derwent Publications Ltd., London, J,A, 0187289 (Honshu Paper Mfg KK), Nov. 17, 1982. (Abstract). 1982.*

Abstract of Patent, JA 0187289 (Honsho Paper Mfg KK), Nov. 17, 1982 (Abstract). 1982.*

Abstract of Patent, JA 0185364 (Ricoh KK), Nov. 15, 1982 (Abstract). 1982.*

Derwent Publications, Ltd., London J5 7139146 (Showa Kako KK) Aug. 27, 1982 (abstract). 1982.*

Abstract of Patent, JA 0090069 (Canon KK), Jun. 4, 1982 (Abstract). 1982.*

Derwent Publications, Ltd., London, JA 0061785 (Nippon Senka KK), Apr. 14, 1982 (Abstract). 1982.*

Fischer, "Submicroscopic contact imaging with visible light by energy transfer", *Appl. Phys. Letter*, 40(3), 1982, no month available.*

Abstract of Patent, JA 0010659 (Canon KK), Jan. 20, 1982 (Abstract). 1982.*

Abstract of Patent, JA 0010661 (Canon KK), Jan. 20, 1982 (Abstract). 1982.*

Christen, "Carbonylverbindungen: Aldehyde und Ketone," *Grundlagen der Organischen Chemie*, 255, 1982, no month available.*

Derwent Publications Ltd., London, J,A, 0155263 (Canon KK), Dec. 1, 1981. (Abstract). 1981.*

Abstract of Patent, JA 0155263 (Canon KK), Dec. 1, 1981 (Abstract). 1981.*

Abstract of Patent, JA 0147861 (Canon KK), Nov. 17, 1981 (Abstract). 1981.*

Derwent Publications Ltd., London, J,A, 0143273 (Canon KK), Nov. 7, 1981. (Abstract). 1981.*

Abstract of Patent, JP 56143272 (Canon KK), Nov. 7, 1981 (Abstract). 1981.*

Abstract of Patent, JA 0136861 (Canon KK), Oct. 26, 1981 (Abstract). 1981.*

Abstract of Patent, JA 6133378 (Canon KK), Oct. 19, 1981 (Abstract). 1981.*

Abstract of Patent, JA 6133377 (Canon KK), Oct. 19, 1981 (Abstract). 1981.*

Abstract of Patent, JA 6093775 (Canon KK), Jul. 29, 1981 (Abstract). 1981.*

Derwent Publications Ltd., London, J,A, 0008135 (Ricoh KK), Jan. 27, 1981. (Abstract). 1981.*

Derwent Publications Ltd., London, J,A, 0004488 (Canon KK), Jan. 17, 1981. (Abstract). 1981.*

Abstract of Patent, JA 0004488 (Canon KK), Jan. 17, 1981 (Abstract). 1981.*

Kirk–Othmer, "Metallic Coatings," *Encyclopedia of Chemical Technology*, 15, 241–274, 1981, no month available.*

Komiyama et al., "One–Pot Preparation of 4–Hydroxychalcone β–Cyclodextrin as Catalyst," *Makromol. Chem.*, 2, 733–734, 1981, no month available.*

Derwent Publications, Ltd., London CA 1086–719 (Sherwood Medical) Sep. 30, 1980 (abstract). 1980.*

Rosanske et al., "Stoichiometric Model of Cyclodextrin Complex Formation", *Journal of Pharmaceutical Sciences*, 69(5), 546–567, 1980, no month available.*

Semple et al., "Synthesis of Functionalized Tetrahydrofurans," *Tetrahedron Letters*, 81, pp. 4561–4564, 1980, no month available.*

Kirk–Othmer, "Film Deposition Techniques," *Encyclopedia of Chemical Technology*, 10, 247–283, 1980, no month available.*

Derwent World Patents Index, Derwent Info. Ltd., JP 54158941 (Toyo Pulp KK), Dec. 15, 1979. (Abstract). 1979.*

Derwent World Patents Index, JP 54117536 (Kawashima F) Sep. 12, 1979. 1979.*

Derwent Publications Ltd., London, J,A, 0005422 (Fuji Photo Film KK), Jan. 16, 1979. (Abstract). 1979.*

Drexhage et al., "Photo–bleachable dyes and processes", *Research Disclosure*, 85–87, 1979, no month available.*

"Color imaging devices and color filter arrays using photo–bleachable dyes", *Research Disclosure*, 22–23, 1979, no month available.*

Wolff, N.E., et al., "Electrophotography", *Kirk–Othmer Encyclopedia of Chemical Technology*, 8, 794–826, 1979, no month available.*

Derwent Publications Ltd., London, J,A, 0012037 (Pentel KK), Jan. 29, 1977. (Abstract). 1977.*

Abstract of Patent, JA 0012037 (Pentel KK), Jan. 29, 1977 (Abstract). 1977.*

Jenkins, P.W. et al., "Photobleachable dye material", *Research Disclosure*, 18 [No. 12932], 1975, no month available.*

Lamberts, R.L., "Recording color grid patterns with lenticules", *Research Disclosure*, 18–19 [No. 12923], 1975, no month available.*

Karmanova, L.S. et al., "Light stabilizers of daytime fluorescent paints", *Chemical Abstracts*, 82, 147 [No. 59971p], 1975, no month available.*

Prokopovich, B. et al., "Selection of effective photoinducers for rapid hardening of polyester varnish PE–250", *Chemical Abstracts*, 83, 131 [No. 81334a], 1975, no month available.*

"Variable Contrast Printing System", *Research Disclosure*, 19 [No. 12931], 1975, no month available.*

Lakshman, "Electronic Absorption Spectrum of Copper Formate Tetrahydrate", *Chemical Physics Letters*, 31(2), 331–334, 1975, no month available.*

Derwent Publications, Ltd., London J4 9131–226 (TNational Cash Register C) Dec. 16, 1974 (abstract). 1974.*

Chang, I.F., et al., "Color Modulated Dye Ink Jet Printer", *IBM Technical Disclosure Bulletin*, 17(5), 1520–1521, 1974, no month available.*

"Darocur 1173: Liquid Photoiniator for Ultraviolet Curing of Coatings", 1974, no month available.*

Hosokawa et al., "Ascofuranone, an antibiotic from Ascochyta," Japan Kokai 73 91,278 (Nov. 28, 1973), *Merck Index*, 80, p. 283; abstract 94259t, 1974.*

Abstract of patent, NL 7112489 (Dec. 27, 1971). 1971.*

Gafney et al., "Photochemical Reactions of Copper (II)—1,3–Diketonate Complexes", *Journal of the Americqal Chemical Society*, 1971, no month available.*

Derwent Publications, Ltd., London SU 292698–S Jan. 15, 1971 (abstract). 1971.*

Derwent World Patents Index,CS 120380 (Kocourek, Jan) Oct. 15, 1966. 1966.*

Rigdon, J.E., "In Search of Paper that Spies Can't Copy", *Wall Street Journal*, no date available.*

Chatterjee,S. et al., "Photochemistry of Carbocyanine Alkyltriphenylborate Salts: Intra–Ion–Pair Electron Transfer and the Chemistry of Boranyl Radicals",*J. Am. Chem. Soc.*, 112, 6329–6338, no date available.*

"Assay—Physical and Chemical Analysis of Complexes", *AMAIZO*, no date available.*

"Cyclodextrin", *AMAIZO*, no date available.*

"Beta Cyclodextrin Polymer (BCDP)", *AMAIZO*, no date available.*

"Chemically Modified Cyclodextrins", *AMAIZO*, no date available.*

"Cyclodextrin Complexation", *American Maize Products Co.*, no date available.*

"Monomers", *Scientific Polymer Products Inc.*, no date available.*

Suppan, Paul, "Quenching of Excited States", *Chemistry and Light*, 65–69, no date available.*

Yamaguchi, H. et al., "Supersensitization. Aromatic ketones as supersensitizers", *Chemical Abstracts*, 53, 107 (d), no date available.*

Stecher, H., "Ultraviolet–absorptive additives in adhesives, lacquers and plastics", *Chemical Abstracts*, 53, 14579 (c), no date available.*

Maslennikov, A.S., "Coupling of diazonium salts with ketones", *ChemicalAbstracts*, 60, 3128e, no date available.*

Derwent Publications Ltd., London, 4 9128022, no date available.*

Abstract of Patent, JP 405195450, no date available.*

Rose, Philip I., "Gelatin," *Encyclopedia of Chemical Technology*, 7, 488–513, no date available.*

* cited by examiner

COLORANT STABILIZERS

CROSS-REFERENCE TO RELATED PATENT APPLICATION

This patent application is a divisional patent application of U.S. patent application Ser. No. 08/903,911, filed Jul. 31, 1997, now U.S. Pat. No. 5,891,229, which is a continuation-in-part patent application of U.S. patent application Ser. No. 08/843,410, filed Apr. 15, 1997, now U.S. Pat. No. 5,855,655, which is a continuation-in-part patent application of U.S. patent application Ser. No. 08/788,863, filed Jan. 23, 1997, now pending, which is a continuation-in-part patent application of U.S. patent application Ser. No. 08/757,222, filed Nov. 27, 1996, now U.S. Pat. No. 5,782,963, which is a continuation-in-part patent application of U.S. patent application Ser. No. 08/627,693, filed Mar. 29, 1996, now abandoned, all of which are incorporated herein by reference.

TECHNICAL FIELD

The present invention relates to a family of colorant stabilizers. The colorant stabilizers, according to the present invention, are capable of stabilizing a colorant when it is exposed to electromagnetic radiation. The colorant stabilizers enable the production of an ink set wherein each ink of the ink set, regardless of color, possesses substantially similar light fastness properties.

BACKGROUND OF THE INVENTION

A major problem with colorants is that they tend to fade when exposed to electromagnetic radiation such as sunlight or artificial light and the like. It is believed that most of the fading of colorants when exposed to light is due to photodegradation mechanisms. These degradation mechanisms include oxidation or reduction of the colorants depending upon the environmental conditions in which the colorant is placed. Fading of a colorant also depends upon the substrate upon which they reside.

Product analysis of stable photoproducts and intermediates has revealed several important modes of photodecomposition. These include electron ejection from the colorant, reaction with ground-state or excited singlet state oxygen, cleavage of the central carbon-phenyl ring bonds to form amino substituted benzophenones, such as triphenylmethane dyes, reduction to form the colorless leuco dyes and electron or hydrogen atom abstraction to form radical intermediates.

Various factors such as temperature, humidity, gaseous reactants, including $O_2$, $O_3$, $SO_2$, and $NO_2$, and water soluble, nonvolatile photodegradation products have been shown to influence fading of colorants. The factors that effect colorant fading appear to exhibit a certain amount of interdependence. It is due to this complex behavior that observations for the fading of a particular colorant on a particular substrate cannot be applied to colorants and substrates in general.

Under conditions of constant temperature it has been observed that an increase in the relative humidity of the atmosphere increases the fading of a colorant for a variety of colorant-substrate systems (e.g., McLaren, K., *J. Soc. Dyers Colour,* 1956, 72, 527). For example, as the relative humidity of the atmosphere increases, a fiber may swell because the moisture content of the fiber increases. This aids diffusion of gaseous reactants through the substrate structure.

The ability of a light source to cause photochemical change in a colorant is also dependent upon the spectral distribution of the light source, in particular the proportion of radiation of wavelengths most effective in causing a change in the colorant and the quantum yield of colorant degradation as a function of wavelength. On the basis of photochemical principles, it would be expected that light of higher energy (short wavelengths) would be more effective at causing fading than light of lower energy (long wavelengths). Studies have revealed that this is not always the case. Over 100 colorants of different classes were studied and found that generally the most unstable were faded more efficiently by visible light while those of higher lightfastness were degraded mainly by ultraviolet light (McLaren, K., *J. Soc. Dyers Colour,* 1956, 72, 86).

The influence of a substrate on colorant stability can be extremely important. Colorant fading may be retarded or promoted by some chemical group within the substrate. Such a group can be a ground-state species or an excited-state species. The porosity of the substrate is also an important factor in colorant stability. A high porosity can promote fading of a colorant by facilitating penetration of moisture and gaseous reactants into the substrate. A substrate may also act as a protective agent by screening the colorant from light of wavelengths capable of causing degradation.

The purity of the substrate is also an important consideration whenever the photochemistry of dyed technical polymers is considered. For example, technical-grade cotton, viscose rayon, polyethylene, polypropylene, and polyisoprene are known to contain carbonyl group impurities. These impurities absorb light of wavelengths greater than 300 nm, which are present in sunlight, and so, excitation of these impurities may lead to reactive species capable of causing colorant fading (van Beek, H. C. A., *Col. Res. Appl.,* 1983, 8(3), 176).

Therefore, there exists a need for methods and compositions which are capable of stabilizing a wide variety of colorants from the effects of both sunlight and artificial light.

SUMMARY OF THE INVENTION

The present invention addresses the needs described above by providing compositions and methods for stabilizing colorants against radiation including radiation in the visible wavelength range.

The present invention also relates to colorant compositions having improved stability, wherein the colorant is associated with a colorant stabilizer. In one embodiment, the colorant stabilizer comprises one or more porphines that have an extremely short triplet state lifetime. (See e.g., Kubát, et al., Photophysical properties of metal complexes of meso-tetrakis (4-sulphonatophenyl) porphyrin, *J. Photochem. and Photbio. A: Chemistry* 96 (1996), pgs 93–97 which is incorporated herein by reference). Particularly suitable porphines include, but are not limited to, porphines having the following structure:

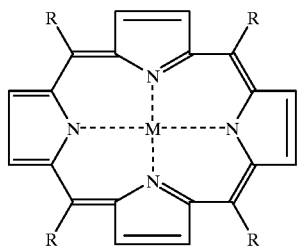

wherein R is any proton-donating moiety and M is iron, cobalt or copper. Desirably, R is SO$_3$H,

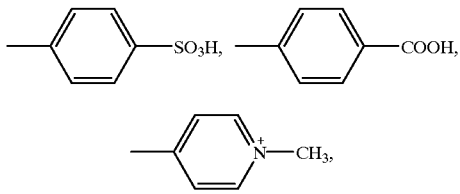

COOH, or R$_1$COOH wherein R$_1$ is an alkyl group of from 1 to 6 carbons.

Examples of such porphines are Cu-meso-tetra-(4-sulfanatophenyl)-porphine (designated CuTPPS4) and Cu-meso-tetra-(N-methyl-4-pyridyl)-porphine, having the following structures:

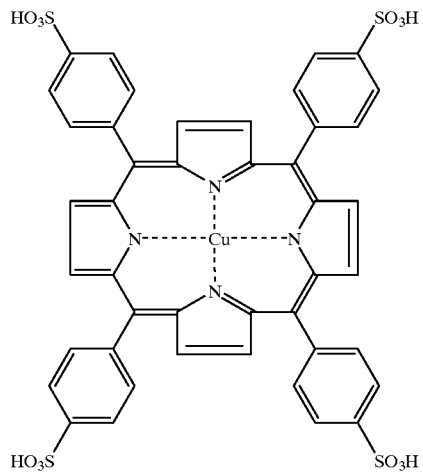

and

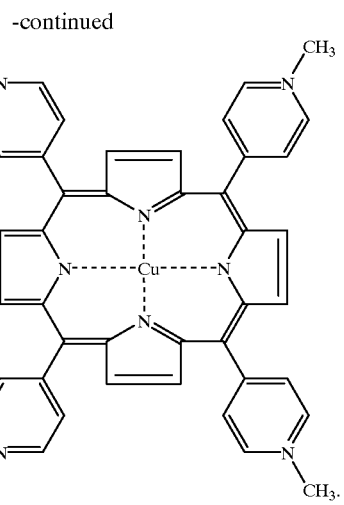

The copper ion can also be substituted with an iron or cobalt ion. Other metal ions can be substituted in the porphine molecule as long as the molecule has a relatively short-lived triplet state.

In a further embodiment of the present invention, the colorant stabilizer comprises at least one porphine in combination with at least one metal or metal salt. Unexpectedly, it has been discovered that the incorporation of a relatively small concentration of metal or metal salt into a porphine-containing composition results in superior colorant stability. Preferred metals or metal salts include, but are not limited to, lanthanides and lanthanide salts. Lanthanide elements include scandium, yttium, lanthanum, cerium praseodymium, neodymium, promethium, samarium, europium, gadolinium, terbium, dysprosium, holmium, erbium, thulium, ytterbium, and lutetium.

In order to improve the solubility of the metal or metal salt in solution, metal solubility-enhancing agents may be added. Particularly useful metal solubility-enhancing agents include, but are not limited to, chelating agents. Optionally, a surfactant can be added to the metal/porphine composition to increase the interaction of the metal or metal salt and the porphine. In addition to surfactants, other additives such as TINUVIN® compounds (Ciba-Geigy Corporation) may be incorporated into the colorant composition.

The substrates to which the colorant stabilizers are applied include, but are not limited to, paper, wood, a wood product or composite, woven fabric, nonwoven fabric, textile, plastic, glass, metal, or any other substrate that would benefit from having a stabilized colorant thereon.

In another embodiment, a colorant stabilizer is present in a polymer coating of a heat transfer product, such as is used for transferring graphic images onto clothing.

Accordingly, each of the embodiments of the present invention provide stabilizing molecules that, when one or more of the stabilizing molecules are associated with a colorant, stabilizes the colorant. Therefore, the stabilizing molecules can be used as an additive to any colorant composition. For example, as certain of the stabilizing molecules are poorly soluble in water, they can be directly added to solvent or oil based (not water based) colorant compositions. Additionally, the stabilizing molecules can be added to other colorant compositions that contain additives enabling the solubilization of the stabilizing molecule therein. Further, the stabilizing molecules can be solubilized in an aqueous solution by attaching the molecule to a large water soluble molecule, such as a cyclodextrin.

The colorant stabilizers are particularly effective in ink jet inks. Use of the colorant stabilizers, as described herein, intensifies the colors and stabilizes the colors when exposed to light. Additionally, the colorant stabilizers are particularly effective in paper such as ink jet paper. Use of the colorant stabilizers in a substrate, as described herein, stabilizes a colorant to which it is applied. Also, colorant stabilizers in a substrate has been found to have the unexpected result of reducing the yellowing of the substrate itself upon exposure to light.

The colorant stabilizers are of particular interest in the formation of ink sets, wherein each ink of the ink set, regardless of color, possesses substantially identical light fastness properties as the other inks in the ink set. The ink set enables the production of multi-color text and/or graphics, which uniformly retain their color over extended periods of time and/or upon extended exposure to light.

These and other features and advantages of the present invention will become apparent after a review of the following detailed description of the disclosed embodiments and the appended claims.

DETAILED DESCRIPTION OF THE INVENTION

This application is directed to compositions and methods for stabilizing colorants against radiation including radiation in the visible wavelength range. This application is further directed to ink sets comprising one or more inks, each of which possesses substantially identical light stability upon exposure to radiation, including radiation in the visible wavelength range. The compositions and methods relating to stabilizing a colorant by admixing a stabilizing molecule with a colorant solution will first be addressed below. Subsequently, the compositions and methods relating to stabilizing a colorant by applying the colorant to a treated substrate containing a stabilizing molecule will be discussed.

As used herein, the term "composition" and such variations as "colored composition" are used herein to mean a colorant and one or more colorant stabilizers of the present invention. The composition can optionally include a molecular includant.

As used herein, the term "colorant" is meant to include, without limitation, any material which typically will be an organic material, such as an organic colorant or dye. The term is meant to include a single material or a mixture of two or more materials.

The term "light-stable" is used herein to mean that the colorant, when associated with one of the colorant stabilizing molecules of the present invention, is more stable to electromagnetic radiation, including, but not limited to, sunlight or artificial light, than when the colorant is not associated with such a compound.

The term "molecular includant," as used herein, is intended to mean any substance having a chemical structure which defines at least one cavity. That is, the molecular includant is a cavity-containing structure. As used herein, the term "cavity" is meant to include any opening or space of a size sufficient to accept at least a portion of the colorant.

The term "functionalized molecular includant" is used herein to mean a molecular includant to which one or more molecules of a colorant stabilizer are covalently coupled to each molecule of the molecular includant. The term "degree of substitution" is used herein to refer to the number of these molecules or leaving groups (defined below) which are covalently coupled to each molecule of the molecular includant.

The term "derivatized molecular includant" is used herein to mean a molecular includant having more than two leaving groups covalently coupled to each molecule of molecular includant. The term "leaving group" is used herein to mean any leaving group capable of participating in a bimolecular nucleophilic substitution reaction. Examples of molecular includants include, but are not limited to, the cyclodextrins.

The term "artificial light" is used herein to mean light having a relatively broad bandwidth that is produced from conventional light sources, including, but not limited to, conventional incandescent light bulbs and fluorescent light bulbs.

The term "thereon" is used herein to mean thereon or therein. For example, the present invention includes a substrate having a colored composition thereon. According to the definition of "thereon" the colored composition may be present on the substrate or it may be in the substrate.

Admixing Stabilizing Molecules Into Colorant Solutions.

The present invention relates to colorant compositions having improved stability, wherein the colorant stabilizer is associated with a colorant solution. Desirably, the colorant stabilizer is admixed with a colorant solution. The colorant stabilizer is desirably one or more porphines alone or in combination with at least one metal or metal salt. The colorant stabilizers of the present invention are admixed with a colorant to stabilize the colorant when the admixture is exposed to electromagnetic radiation such as artificial light or sunlight.

The present invention further relates to a method of stabilizing a colorant comprising associating one or more of the colorant stabilizers with the colorant solution. Optionally, the colorant stabilizer may be associated with a molecular includant, chelating agent, or other material to improve solubility and/or interaction of the colorant stabilizer and the colorant.

The present invention is particularly useful for stabilizing inks to be used in ink jet printers. Inks used in ink jet printers are described in U.S. patent application Ser. No. 08/769,885 filed on Dec. 19, 1996, now U.S. Pat. No. 5,681,380, which is a continuation of U.S. patent application Ser. No. 08/461,382 filed on Jun. 5, 1995, now abandoned, which is a divisional of U.S. patent application Ser. No. 08/461,365 filed on Jun. 5, 1995, now abandoned, all of which are incorporated herein by reference.

In another embodiment of the present invention, a colorant stabilizer is represented by porphines having an extremely short triplet state lifetime. (See e.g., Kubát, et al., Photophysical properties of metal complexes of meso-tetrakis (4-sulphonatophenyl) porphyrin, *J. Photochem. and Photbio. A: Chemistry* 96 (1996), pgs 93–97 which is incorporated herein by reference). Particularly suitable porphines include, but are not limited to, porphines having the following structure:

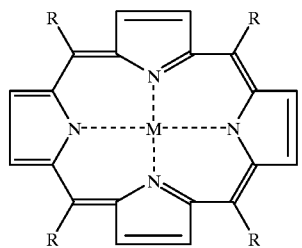

wherein R is any proton-donating moiety and M is iron, cobalt or copper. Desirably, R is SO₃H,

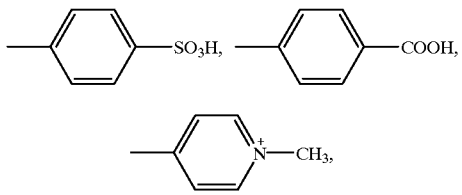

COOH, or R₁COOH wherein R₁ is an alkyl group of from 1 to 6 carbons.

Desirably, the colorant stabilizer is represented by the porphines Cu-meso-tetra-(4-sulfanatophenyl)-porphine (designated CuTPPS4) and Cu-meso-tetra-(N-methyl-4-pyridyl)-porphine (designated CuTMPS4), having the following structure:

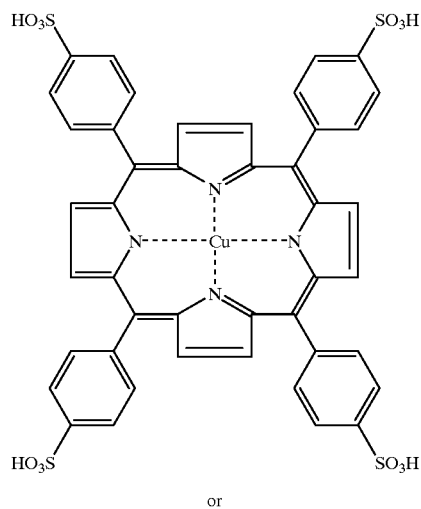

or

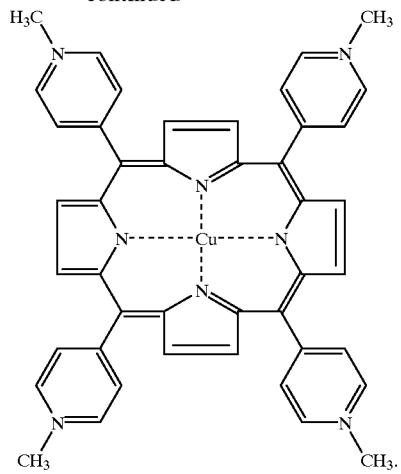

The copper ion can also be substituted with an iron or cobalt ion. It is also understood that in the case of FeTPPS4, CuTPPS4 or CoTPPS4, the sulfuric acid moieties may be substituted with salts when in solution, such as sodium salts. The colorant solution may be stabilized with about 0.1% to 10% wt/wt porphine, more preferably about 0.3% to 1% wt/wt porphine, and more preferably about 0.5% wt/wt porphine.

In another embodiment, the colorant stabilizer comprises one or more porphines in combination with one or more metals or metal salts, such as lanthanides and lanthanide salts. Desirably, the amount of metal or metal salt in the colorant solution is from about 0.01% to 10% wt/wt metal, more desirably about 0.03% to 1% wt/wt metal, and more desirably about 0.05% wt/wt metal. Although lanthanides and lanthanide salts are desired metals, other metals, may also be used such as magnesium, iron, zinc, and other transition metals. To improve the solubility of the metal or metal salt in solution, metal solubility-enhancing agents may be added. Particularly useful metal solubility-enhancing agents include, but are not limited to, chelating agents, including, but not limited to, EDTA (ethylenediaminetetraacetic acid) or EGTA (ethylene glycol-bis(β-aminoethyl ether)).

In a further embodiment, the colorant stabilizer comprises a porphine and a lanthanide, such as europium. Desirably, the amount of porphine in the colorant solution is from about 0.1% to 10% wt/wt porphine, more desirably about 0.3% to 1% wt/wt porphine, and more desirably about 0.5% wt/wt porphine. Desirably, the amount of lanthanide in the colorant solution is from about 0.01% to 10% wt/wt lanthanide, more desirably about 0.03% to 1% wt/wt lanthanide, and more desirably about 0.05% wt/wt lanthanide. Although europium and europium salts are desired lanthanides, other lanthanides, may also be used.

Although not wanting to be limited by the following, it is theorized that the above stabilizing compounds of the present invention, either admixed with a colorant solution or on or in a substrate to which the colorant is applied, act by quenching the excited state of a dye molecule by efficiently returning it to a ground state. This reduces the likelihood of an oxidative or other chemical reaction occurring which would render the dye chromophore colorless.

The quenching process can occur by a number of processes. One such process is referred to as the heavy atom effect (internal or external) in which atoms with a high atomic number, such as iodine, xenon and lanthanides, can effect the excited electronic transitions of the dye molecule by allowing here to fore forbidden electronic transitions to occur and by decreasing the excited state lifetimes. This effect permits the rapid return of the dye to its ground state.

Another quenching process involves back electron transfer. In this case, quenching of the excited dye molecule occurs through sequential electron transfer. The additive or quencher, and dye form an ion pair through electron donation within which back electron transfer leads to an overall deactivation of the excited energy donor, i.e., the dye.

Another quenching process involves a condition in which the quencher (additive) molecule has an excited energy state lower than the excited dye. In this case, it may be possible to transfer the excited energy to the quencher thereby allowing the dye molecule to return to its ground state. These mechanisms are more fully discussed in *Chemistry and Light,* Suppan, P., Published by The Royal Society of Chemistry, 1994, pgs 65–69 which is incorporated herein by reference.

The dye or colorant, for example, may be an organic dye. Organic dye classes include, by way of illustration only, triarylmethyl dyes, such as Malachite Green Carbinol base {4-(dimethylamino)-α-[4-(dimethylamino)phenyl]-α-phenyl-benzene-methanol}, Malachite Green Carbinol hydrochloride {N-4-[[4-(dimethylamino)phenyl]phenyl-methylene]-2,5-cyclohexyldien-1-ylidene]-N-methyl-methanaminium chloride or bis[p-(dimethylamino)phenyl] phenylmethylium chloride}, and Malachite Green oxalate {N-4-[[4-(dimethylamino)phenyl]-phenylmethylene]-2,5-cyclohexyldien-1-ylidene]-N-methyl-methanaminium chloride or bis[p-(dimethylamino)phenyl]phenylmethylium oxalate}; monoazo dyes, such as Cyanine Black, Chrysoidine [Basic Orange 2; 4-(phenylazo)-1,3-benzenediamine monohydrochloride], Victoria Pure Blue BO, Victoria Pure Blue B, basic fuschin and β-Naphthol Orange; thiazine dyes, such as Methylene Green, zinc chloride double salt [3,7-bis (dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazinocarbonyl)amino]-2, 3-dihydro-1,3-dioxo-1H-benz[de]isoquinoline-5,8-disulfonic acid dilithium salt}; azine dyes, such as Janus Green B {3-(diethylamino)-7-[[4-(dimethylamino)phenyl] azo]-5-phenylphenazinium chloride}; cyanine dyes, such as Indocyanine Green {Cardio-Green or Fox Green; 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methylcoumarin (4-methylumbelliferone); benzimidazole dyes, such as Hoechst 33258 [bisbenzimide or 2-(4-hydroxyphenyl)-5-(4-methyl-1-piperazinyl)-2,5-bi-1H-benzimidazole trihydrochloride pentahydrate]; paraquinoidal dyes, such as Hematoxylin {Natural Black 1; 7,11b-dihydrobenz[b]-indeno[1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxybenzene diazonium chloride, zinc chloride double salt); phenylenediamine dyes, such as Disperse Yellow 9 [N-(2,4-dinitrophenyl)-1,4-phenylenediamine or Solvent Orange 53]; diazo dyes, such as Disperse Orange 13 [Solvent Orange 52; 1-phenylazo-4-(4-hydroxyphenylazo) naphthalene]; anthraquinone dyes, such as Disperse Blue 3 [Celliton Fast Blue FFR; 1-methylamino-4-(2-hydroxyethylamino)-9,10-anthraquinone], Disperse Blue 14 [Celliton Fast Blue B; 1,4-bis(methylamino)-9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-1-hydroxy-3-sulfo-2-naphthalenyl)azo]-6-sulfo-1-naphthalenyl)azo]-1-naphthalenyl)azo]-1,5-naphthalenedisulfonic acid tetrasodium salt}; xanthene dyes, such as 2,7-dichlorofluorescein; proflavine dyes, such as 3,6-diaminoacridine hemisulfate (Proflavine); sulfonaphthalein dyes, such as Cresol Red (o-cresolsulfonaphthalein); phthalocyanine dyes, such as Copper Phthalocyanine {Pigment Blue 15; (SP-4-1)-[29H,31H-phthalocyanato(2-)-$N^{29}$, $N^{30},N^{31},N^{32}$]copper}; carotenoid dyes, such as trans-β-carotene (Food Orange 5); carminic acid dyes, such as Carmine, the aluminum or calcium-aluminum lake of carminic acid (7-a-D-glucopyranosyl-9,10-dihydro-3,5,6,8-tetrahydroxy-1-methyl-9,10-dioxo-2-anthracenecarbonylic acid); azure dyes, such as Azure A [3-amino-7-(dimethylamino)phenothiazin-5-ium chloride or 7-(dimethylamino)-3-imino-3H-phenothiazine hydrochloride]; and acridine dyes, such as Acridine Orange [Basic Orange 14; 3,8-bis(dimethylamino)acridine hydrochloride, zinc chloride double salt] and Acriflavine (Acriflavine neutral; 3,6-diamino-10-methylacridinium chloride mixture with 3,6-acridinediamine).

In some embodiments of the present invention, the colorant and/or colorant stabilizer is associated with a molecular includant. The term "associated" in its broadest sense means that the colorant and/or colorant stabilizer is at least in close proximity to the molecular includant. For example, the colorant and/or colorant stabilizer may be maintained in close proximity to the molecular includant by hydrogen bonding, van der Waals forces, or the like. Alternatively, the colorant and/or colorant stabilizer may be covalently bonded to the molecular includant, although this normally is neither desired nor necessary. As a further example, the colorant and/or colorant stabilizer may be at least partially included within the cavity of the molecular includant.

The molecular includant can be added to the colorant solution or incorporated into a substrate, such as paper, which is subsequently coated with the colorant solution. The molecular includant can be inorganic or organic in nature. In certain embodiments, the chemical structure of the molecular includant is adapted to form a molecular inclusion complex. Examples of molecular includants are, by way of illustration only, clathrates or intercalates, zeolites, and cyclodextrins. Examples of cyclodextrins include, but are not limited to, α-cyclodextrin, β-cyclodextrin, γ-cyclodextrin, δ-cyclodextrin, hydroxypropyl β-cyclodextrin, hydroxyethyl β-cyclodextrin, hydroxyethyl α cyclodextrin, carboxymethyl α cyclodextrin, carboxymethyl β cyclodextrin, carboxymethyl γ cyclodextrin, octyl succinated α cyclodextrin, octyl succinated β cyclodextrin, octyl succinated y cyclodextrin and sulfated β cyclodextrin and sulfated γ-cyclodextrin (Cerestar U.S.A., Incorporated, Hammond, Ind.).

The term "derivatized cyclodextrin" as used herein means a cyclodextrin having more than two leaving groups covalently coupled to each molecule of cyclodextrin. The term "leaving group" is used herein to mean any leaving group capable of participating in a bimolecular nucleophilic substitution reaction. Examples of derivatized cyclodextrin includes, but is not limited to, hydroxypropyl β-cyclodextrin, hydroxyethyl β-cyclodextrin, hydroxyethyl α cyclodextrin, carboxymethyl α cyclodextrin, carboxymethyl β cyclodextrin, carboxymethyl γ cyclodextrin, octyl succinated α cyclodextrin, octyl succinated β cyclodextrin, octyl succinated γ cyclodextrin and sulfated β and γ-cyclodextrin. A desired derivatized cyclodextrin is ethyl-hydroxy β-cyclodextrin.

A desired molecular includant is γ-cyclodextrin. Another desirable molecular includant is β-cyclodextrin. In other embodiments, the molecular includant is an ethyl hydroxy β-cyclodextrin. Although not wanting to be bound by the following theory, it is believed that the molecular includant inhibits the aggregation of the colorant molecule in solution. Other aggregation inhibitors that can be used in practicing the present invention are starches, pectins, amyloses, clathrates and the crown ethers. It is to be understood that the addition of derivatized cyclodextrins to an ink formulation for the purpose of inhibiting aggregation and/or stabilizing the dyes in the inks is considered one aspect of the present invention.

As a practical matter, the colorant, the colorant stabilizer and molecular includant are likely to be solids depending upon the constituents used to prepare the molecules. However, any or all of such materials can be a liquid. The colored composition can be a liquid either because one or more of its components is a liquid, or, when the molecular includant is organic in nature, a solvent is employed. Suitable solvents include, but are not limited to, amides, such as N,N-dimethylformamide; sulfoxides, such as dimethylsulfoxide; ketones, such as acetone, methyl ethyl ketone, and methyl butyl ketone; aliphatic and aromatic hydrocarbons, such as hexane, octane, benzene, toluene, and the xylenes; esters, such as ethyl acetate; water; and the like. When the molecular includant is a cyclodextrin, particularly suitable solvents are the amides and sulfoxides.

In an embodiment where the composition of the present invention is a solid, the effectiveness of the above compounds on the colorant is improved when the colorant and the selected compounds are in intimate contact or in an association that approaches van der Waals radii. To this end, the thorough blending of the components, along with other components which may be present, is desirable. Such blending generally is accomplished by any of the means known to those having ordinary skill in the art. When the colored composition includes a polymer, blending is facilitated if the colorant and the colorant stabilizer are at least partly soluble in softened or molten polymer. In such case, the composition is readily prepared in, for example, a two-roll mill. Alternatively, the composition of the present invention can be a liquid because one or more of its components is a liquid.

For some applications, the composition of the present invention typically will be utilized in particulate form. In other applications, the particles of the composition should be very small. Methods of forming such particles are well known to those having ordinary skill in the art.

The colored composition optionally may also contain a carrier, the nature of which is well known to those having ordinary skill in the art. For many applications, the carrier will be a polymer, typically a thermosetting or thermoplastic polymer, with the latter being the more common. Examples of suitable thermosetting and thermoplastic polymers are disclosed in parent U.S. patent application Ser. No. 08/843,410, now U.S. Pat. No. 5,855,655, assigned to Kimberly Clark Worldwide, Inc., the entire content of which is hereby incorporated by reference.

In addition to the colorant, colorant stabilizer, and optional molecular includant, the colored composition of the present invention also can contain additional components, depending upon the application for which it is intended. Examples of such additional components include, but are not limited to, charge carriers; stabilizers against thermal oxidation; viscoelastic properties modifiers; cross-linking agents; plasticizers; charge control additives such as a quaternary ammonium salt; flow control additives such as hydrophobic silica, zinc stearate, calcium stearate, lithium stearate, polyvinylstearate, and polyethylene powders; fillers such as calcium carbonate, clay and talc; surfactants; chelating agents; and TINUVIN® compounds; among other additives used by those having ordinary skill in the art. Charge carriers are well known to those having ordinary skill in the art and typically are polymer-coated metal particles. Desirable surfactants include, but are not limited to, $C_{12}$ to $C_{18}$ surfactants such as cetyl trimethyl ammonium chloride and carboxymethylamylose. TINUVIN® compounds are a class of compounds produced by Ciba-Geigy Corporation, which includes benzophenones, benzotriazoles and hindered amines. Desirable TINUVIN® compounds include, but are not limited to, 2-(2'-hydroxy-3'-sec-butyl-5'-tert-butylphenyl)-benzotriazole, poly-(N-β-hydroxyethyl-2,2,6,6-tetramethyl-4-hydroxy-piperidyl succinate and 2-(2'-hydroxy-3',5'-ditert butylphenyl)-5-chloro-benzotriazole. The identities and amounts of such additional components in the colored composition are well known to one of ordinary skill in the art.

When the colorant stabilizers of the present invention are used to stabilize the dyes in ink jet inks, it is desirable to filter the compositions through a small pore filter ($0.45\mu$) such as a Millipore® filter before the ink formulation is placed in an ink jet cartridge. This will reduce or eliminate clogging of the cartridge ink nozzles due to particulate matter.

The colorant stabilizers of the present invention enable the formation of ink sets comprising one or more inks, wherein each ink of the ink set, regardless of color, possesses similar light fastness properties as the other inks in the ink set. Such ink sets may be used to produce multi-color text and/or graphics, which uniformly retain their color over extended periods of time and/or upon extended exposure to light. One desirable ink set includes cyan, magenta, yellow and black inks, wherein the magenta ink contains colorant stabilizers in the form of a porphine and a metal, such as europium, and the yellow ink contains a colorant stabilizer in the form of a porphine without the metal. Another desirable ink set includes cyan, magenta, yellow and black inks, wherein the cyan ink contains a colorant stabilizer in the form of a benzophenone, and the magenta and yellow inks contain colorant stabilizers in the form of a porphine and a metal, such as europium.

It is to be understood that in any desired ink set, a single ink may be stabilized according to the present invention or several of the inks may be stabilized utilizing one or more of the stabilizing agents described herein. Other ink sets are within the scope of the present invention. Included in the present invention are ink sets wherein the black color is a pigment and the other colors in the ink set are dyes. Although ink sets wherein the inks possess substantially identical light fastness properties are desirable, in some embodiments, it may be desirable to produce ink sets wherein the inks within the ink set have specifically controlled, varying light fastness properties.

The substrates to which the colorant and colorant stabilizers are applied include, but are not limited to, paper, wood, a wood product or composite, woven fabric, nonwoven fabric, textile, plastic, glass, metal, or any other substrate that would benefit from having a stabilized colorant thereon. Examples of suitable substrates are disclosed in parent U.S. patent application Ser. No. 08/843,410, now U.S. Pat. No. 5,855,655, assigned to Kimberly Clark Worldwide, Inc., the entire content of which is hereby incorporated by reference.

The present invention is further described by the examples which follow. Such examples, however, are not to be construed as limiting in any way either the spirit or scope of the present invention. In the examples, all parts are parts by weight unless stated otherwise.

EXAMPLE 1

Preparation and Testing of Inks Containing Porphine Colorant Stabilizers

This example reports the results of fade testing of various inks, either with or without the stabilizing additives of the present invention, on treated or untreated paper. More particularly, the paper is untreated Hewlett-Packard premium paper, or treated Hewlett-Packard premium paper prepared using a solution of about 50% wt/wt hydroxypropyl γ-cyclodextrin to ink, in or on the paper in a concentration of about 5 to 15% wt/wt solution to paper.

The stabilizing additives of this example are porphines. Specifically, the porphines Cu-meso-tetra-(4-sulfanatophenyl)-porphine (designated CuTPPS4) and Cu-meso-tetra-(N-methyl-4-pyridyl)-porphine (designated CuTMPS4) (available from Porphyrin Products, Inc., Logan, Utah) were used, which are represented by the following structures, respectively:

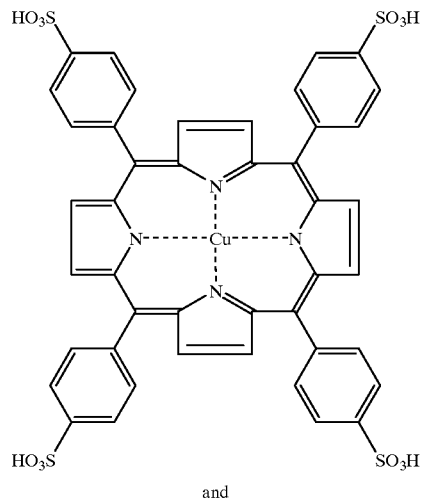

and

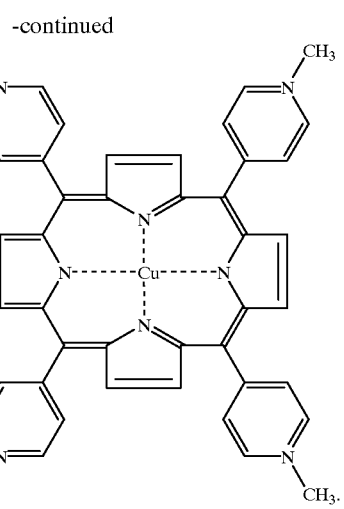

The invention provides that the metal ion Co or Cu may be used interchangeably in the porphine structures of the present invention. Additional background on the chemistry of porphines can be found in Kubat et al. "Photophysical properties of metal complexes of meso-tetrakis (4-sulphonatophenyl) Porphyrin," *Journal of Photochemistry and Photobiology A:Chemistry* 96 (1996) 93–97, and references cited therein, hereby incorporated by reference.

Printed sheets of paper were placed in the Atlas weatherometer and exposed for the designated number of hours under the following conditions: 0.54 W/m$^2$ at 440 nm, 55% humidity, 45° C. black panel temperature, borosilicate filters.

The change in magenta color is measured by the Xrite Colorimeter (Model 938, SpectroDensitometer, Grandville, Michigan) which measures the ΔE* values, based on the L, a*, b* as described by Cielab, D-50-2. The results are reported in the tables below.

The treated and untreated paper is printed with inks designated A1, A2, A3, A4, B1, B2, B3, B4, C1, C2, C3, and C4, prepared as follows:

| | | |
|---|---|---|
| A1 Ink | DI Water | 84.80% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 4.00 |
| | Acid Red 52 | 0.40 |
| A2 Ink | DI Water | 85.40% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 3.00 |
| | Acid Red 52 | 0.80 |
| A3 Ink | DI Water | 86.00% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 2.00 |
| | Acid Red 52 | 1.20 |
| A4 Ink | DI Water | 86.60% |
| | 2 Pyrrolidone | 10.00 |
| | Giv Guard DXN | 00.20 |
| | Cobratec 99 | 00.10 |

-continued

| | | |
|---|---|---|
| | Triethanolamine | 00.50 |
| | Reactive Red 120 | 1.00 |
| | Acid Red 52 | 1.60 |
| B1 Ink | DI Water | 83.02% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 5.78 |
| | Acid Red 52 | 0.40 |
| B2 Ink | DI Water | 84.07% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 4.33 |
| | Acid Red 52 | 0.80 |
| B3 Ink | DI Water | 85.11% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 2.89 |
| | Acid Red 52 | 1.20 |
| B4 Ink | DI Water | 86.16% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 1.44 |
| | Acid Red 52 | 1.60 |
| C1 Ink | DI Water | 82.62% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 6.18 |
| | Acid Red 52 | 0.40 |
| C2 Ink | DI Water | 82.62% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 4.63 |
| | Acid Red 52 | 0.80 |
| C3 Ink | DI Water | 84.91% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 3.09 |
| | Acid Red 52 | 1.20 |
| C4 Ink | DI Water | 86.06% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 1.54 |
| | Acid Red 52 | 1.60 |

The above inks were fade tested with the following results.

Inks Without Additives

| | 63H | |
|---|---|---|
| Ink ID# | ΔE* | ΔH* |
| A1 | 47.8 | 7.5 |
| A2 | 57.5 | 21.6 |
| A3 | 60.7 | 33.8 |
| A4 | 62.1 | 43.2 |
| B1 | 38 | −0.54 |
| B2 | 46.4 | 14.8 |
| B3 | 56.3 | 28.4 |
| B4 | 64.7 | 39.1 |
| C1 | 69.4 | 2.6 |
| C2 | 64.3 | 11.3 |
| C3 | 72.4 | 20.5 |
| C4 | 83.9 | 22.7 |

The inks were prepared with about 0.5% $CuTPPS_4$ stabilizing additive and fade tested on HP paper and HP γ-CD paper with the following results.

Inks made with 0.5% $CuTPPS_4$ on HP premium paper

| Samples | 15H | | 78H | | 94H | |
|---|---|---|---|---|---|---|
| ID# | ΔE* | ΔH* | ΔE* | ΔH* | ΔE* | ΔH* |
| A1 | 9.6 | 4.8 | 34.7 | 12.1 | 41.6 | 12.8 |
| A2 | 14.7 | 12.8 | 41.8 | 23.8 | 48.8 | 24.9 |
| A3 | 19.6 | 18.7 | 42.7 | 31.9 | 47 | 32.7 |
| A4 | 29.6 | 28.9 | 51.8 | 42.4 | 55.5 | 42.1 |
| B1 | 8.2 | 1.8 | 30.6 | 8.8 | 38.2 | 9.2 |
| B2 | 8.3 | 6.3 | 32.3 | 17.8 | 37.8 | 18.8 |
| B3 | 14.9 | 13.8 | 39.0 | 27.5 | 44.5 | 28.6 |
| B4 | 25.2 | 24.6 | 47.7 | 38.3 | 51.6 | 38.5 |
| C1 | 14.3 | −7.71 | 41.8 | 8.9 | N/A | N/A |
| C2 | 7.9 | −2.7 | 33.7 | 13.9 | N/A | N/A |
| C3 | 9.2 | 6.9 | 37.9 | 23.6 | N/A | N/A |
| C4 | 23.1 | 22.2 | 48.6 | 37.7 | N/A | N/A |

Inks with 0.5% $CuTPPS_4$ on Hydroxy-Propyl γ-CD paper

| Samples | 15H | | 78H | | 94H | |
|---|---|---|---|---|---|---|
| ID# | ΔE* | ΔH* | ΔE* | ΔH* | ΔE* | ΔH* |
| A1 | 1.5 | −0.2 | 6.6 | −3.2 | 8 | −4.1 |
| A2 | 1.2 | 0.28 | 4.1 | −0.8 | 5.4 | −1.3 |
| A3 | 2.8 | 2.14 | 5 | 4.3 | 5.2 | 4.3 |
| A4 | 4.9 | 4.7 | 10.4 | 9.8 | 10.2 | 9.5 |
| B1 | 3.1 | −1.5 | 9.4 | −5.5 | 11.2 | −6.9 |
| B2 | 2.3 | −2.4 | 7.7 | −5.2 | 8.3 | −5.7 |
| B3 | 1.2 | 1.1 | 4.1 | 0.13 | 4.7 | −0.79 |
| B4 | 2.9 | 2.6 | 7.2 | 6.3 | 7.7 | 6.5 |
| C1 | 4 | −3.3 | 17.1 | −13.8 | N/A | N/A |
| C2 | 3 | −2.6 | 3.4 | −2.8 | N/A | N/A |
| C3 | 1.6 | −1.5 | 5.2 | −3.3 | N/A | N/A |
| C4 | 1.4 | 1.1 | 4.7 | 3.5 | N/A | N/A |

Additionally, HP-1600 magenta ink was prepared with about 0.5% $CuTPPS_4$ stabilizing additive and fade tested on HP paper and HP γ-CD paper with the following results.

15 Hour Multiple Samples

| Samples ID# | ΔE* | ΔH* |
|---|---|---|
| HP#1 | 14.68 | 13.13 |
| HP#2 | 20.86 | 19.50 |
| HP#3 | 17.01 | 15.55 |

-continued

| 15 Hour Multiple Samples | | |
|---|---|---|
| Samples ID# | ΔE* | ΔH* |
| HP#4 | 13.04 | 11.15 |
| HP#5 | 13.11 | 10.57 |
| HP#6 | 13.09 | 11.10 |
| HP γ-CD #1 | 2.66 | -1.47 |
| HP γ-CD #2 | 1.20 | -.53 |
| HP γ-CD #3 | 2.44 | -.53 |
| HP γ-CD #4 | 1.30 | -.47 |
| HP γ-CD #5 | 1.74 | -.30 |
| HP γ-CD #6 | 1.35 | -.34 |

The HP-1600 magenta ink was also prepared with about 0.5% $CuTMPS_4$ stabilizing additive and fade tested on HP paper and HP γ-CD paper with the following results.

| 15 Hour Multiple Samples | | |
|---|---|---|
| HP#1 | 13.94 | 11.39 |
| HP#2 | 13.58 | 11.11 |
| HP#3 | 13.98 | 11.57 |
| HP#4 | 14.16 | 11.56 |
| HP γ-CD #1 | 2.32 | -.99 |
| HP γ-CD #2 | 1.44 | -1.05 |
| HP γ-CD #3 | 2.17 | -.67 |
| HP γ-CD #4 | 1.98 | -1.21 |
| HP γ-CD #5 | 2.14 | -1.38 |
| HP γ-CD #6 | 1.79 | -.85 |
| HP γ-CD #7 | .36 | .15 |

EXAMPLE 2

Preparation and Testing of Inks Containing Porphine and Lanthanide Colorant Stabilizers This example reports the results of fade testing of various inks, either with or without the stabilizing additives of the present invention, on untreated paper. More particularly, the paper is untreated QIS Photo Glossy paper.

The stabilizing additives of this example are porphines and europium salts. Specifically, the porphine Cu-meso-tetra-(4-sulfanatophenyl)-porphine (designated CuTPPS4) (available from Porphyrin Products, Inc., Logan, Utah) is used, as in Example 1 above. The europium salt, europium nitrate (designated EuN) (Strem Chemical Co., Newburyport, Mass.) is used.

A forty-eight hour accelerated fade test of various magenta ink composition was performed. A magenta control without stabilizing additives was applied to the QIS paper medium. After subjecting the ink composition and paper medium to the forty-eight hour test, ΔE* and ΔH* values were measured. Similar measurements were taken using the following ink formulations:
a) magenta+0.5 wt % CuTPPS4
b) magenta+0.05 wt % EuN
c) magenta+0.5 wt % CuTPPS4+0.05 wt % EuN.

The resulting measurements are given below.

| Ink Formulation | Media | ΔE* | ΔH* |
|---|---|---|---|
| Magenta Control | QIS Photo Glossy | 31.8 | 24.5 |
| Magenta + CuTPPS4 | QIS Photo Glossy | 16.4 | -3.7 |

-continued

| Ink Formulation | Media | ΔE* | ΔH* |
|---|---|---|---|
| Magenta + EuN | QIS Photo Glossy | 19.6 | 17.3 |
| Magenta + CuTPPS4 + EuN | QIS Photo Glossy | 7.8 | 2.8 |

Having thus described the invention, numerous changes and modifications thereof will be readily apparent to those having ordinary skill in the art, without departing from the spirit or scope of the invention.

What is claimed is:

1. An ink set comprising two or more inks, wherein one or more inks of the ink set contain at least one colorant stabilizer, wherein the at least one colorant stabilizer comprises a porphine.

2. The ink set of claim 1, wherein the porphine is represented by the following formula

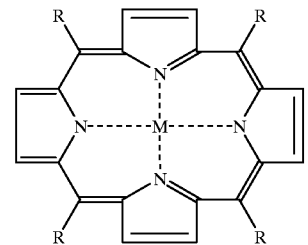

wherein M is iron, cobalt or copper; and wherein R is $SO_3H$,

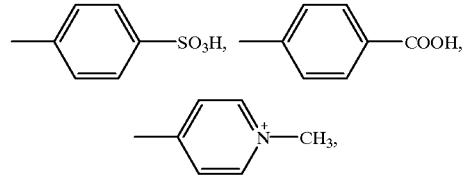

COOH, or $R_1COOH$ wherein $R_1$ is an alkyl group of from 1 to 6 carbons.

3. The ink set of claim 2, wherein the porphine is Cu-meso-tetra-(4-sulfanatophenyl)-porphine or Cu-meso-tetra-(N-methyl-4-pyridyl)-porphine, having the following structures, respectively:

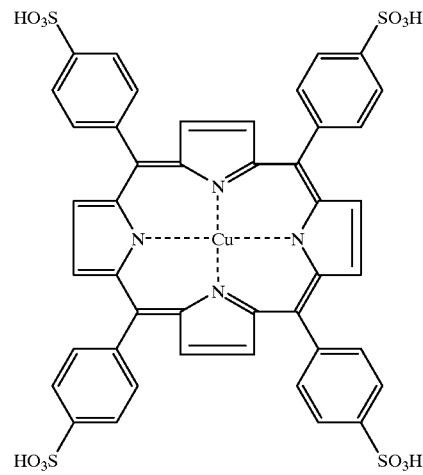

-continued

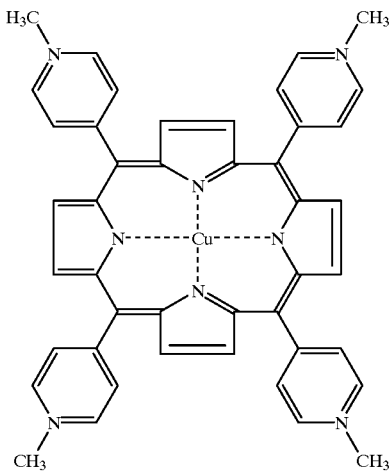

or the porphine is Co-meso-tetra-(4-sulfanatophenyl)-porphine or Co-meso-tetra-(N-methyl-4-pyridyl)-porphine, having the following structures, respectively:

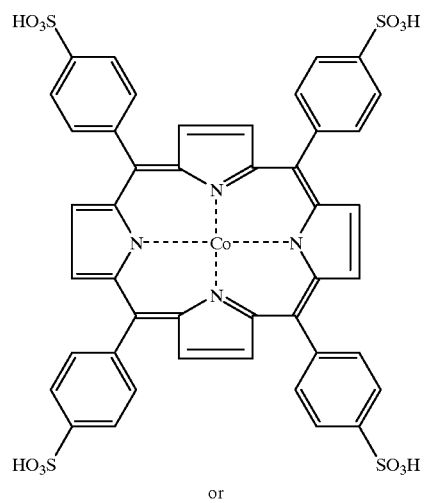

or

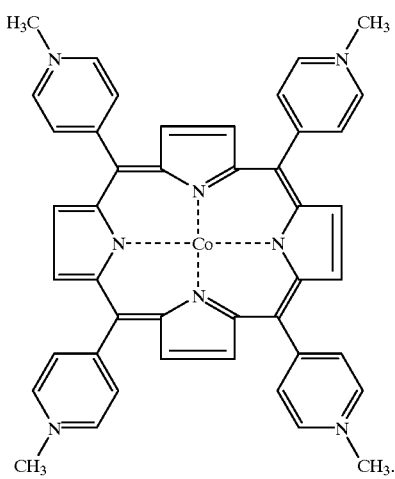

4. The ink set of claim 1, wherein a metal or metal salt is added to the one or more inks containing the porphine.

5. The ink set of claim 4, wherein the metal or metal salt comprises a lanthanide or lanthanide salt.

6. The ink set of claim 5, wherein the lanthanide or lanthanide salt comprises an europium or europium salt.

7. The ink set of claim 1, wherein the porphine is associated with a molecular includant.

8. The ink set of claim 7, wherein the molecular includant is one or more cyclodextrins.

9. The ink set of claim 8, wherein the one or more cyclodextrins comprise α-cyclodextrin, β-cyclodextrin, γ-cyclodextrin, δ-cyclodextrin, hydroxypropyl β-cyclodextrin, or hydroxyethyl β-cyclodextrin.

10. The ink set of claim 1, wherein one or more inks of the ink set contain a colorant, wherein the colorant comprises a triarylmethyl dye, a monoazo dye, a thiazine dye, an oxazine dye, a naphthalimide dye, an azine dye, a cyanine dye, an indigo dye, a coumarin dye, a benzimidazole dye, a paraquinoidal dye, a fluorescein dye, a diazonium salt dye, an azoic diazo dye, a phenylenediamine dye, a diazo dye, an anthra-quinone dye, a trisazo dye, a xanthene dye, a proflavine dye, a sulfonaphthalein dye, a phthalocyanine dye, a carotenoid dye, a carminic acid dye, an azure dye, an acridine dye, or a combination thereof.

11. The ink set of claim 4, wherein the one or more inks containing the metal or metal salt further contains at least one metal solubility-enhancing agent.

12. The ink set of claim 11, wherein the at least one metal solubility-enhancing agent comprises ethylenediaminetetraacetic acid or ethylene glycol-bis(β-aminoethyl ether).

13. The ink set of claim 7, wherein the molecular includant comprises a clathrate or intercalate, a zeolite, a cyclodextrin, or a combination thereof.

14. The ink set of claim 7, wherein the porphine is covalently bonded to the molecular includant.

15. The ink set of claim 1, wherein one or more inks of the ink set contain a solvent, wherein the solvent comprises an amide, a sulfoxide, a ketone, an aliphatic hydrocarbon, an aromatic hydrocarbon, an ester, water, or a combination thereof.

16. The ink set of claim 1, wherein one or more inks of the ink set contain a solvent, wherein the solvent comprises N,N-dimethylformamide; dimethylsulfoxide; acetone; methyl ethyl ketone; methyl butyl ketone; hexane; octane; benzene; toluene; xylene; ethyl acetate; water; or a combination thereof.

17. The ink set of claim 7, wherein the one or more inks containing the molecular includant further contains a solvent, wherein the solvent comprises an amide, a sulfoxide, or water.

18. The ink set of claim 1, wherein each ink of the ink set has a light fastness property, and wherein at least two inks of the ink set have independent light fastness properties which are controlled and differ from one another.

19. A composition comprising a colorant and at least one colorant stabilizer, wherein the at least one colorant stabilizer comprises a porphine.

20. The composition of claim 19, wherein at least one porphine is represented by the following formula

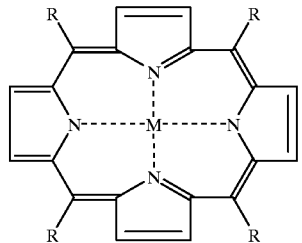

wherein M is iron, cobalt or copper; and wherein R is SO₃H,

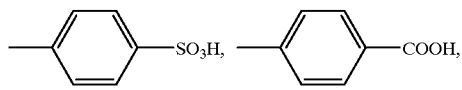

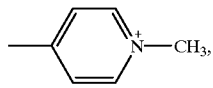

COOH, or R₁COOH wherein R₁ is an alkyl group of from 1 to 6 carbons.

21. The composition of claim 20, wherein at least one porphine is Cu-meso-tetra-(4-sulfanatophenyl)-porphine or Cu-meso-tetra-(N-methyl-4-pyridyl)-porphine, having the following structures, respectively:

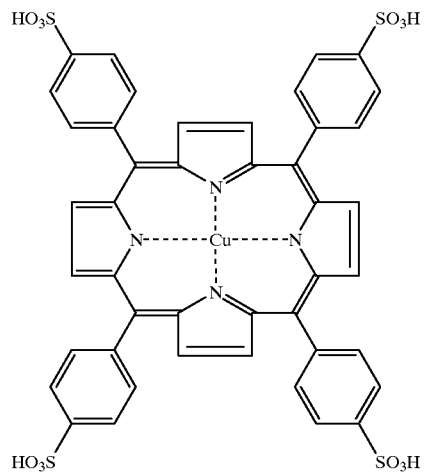

or

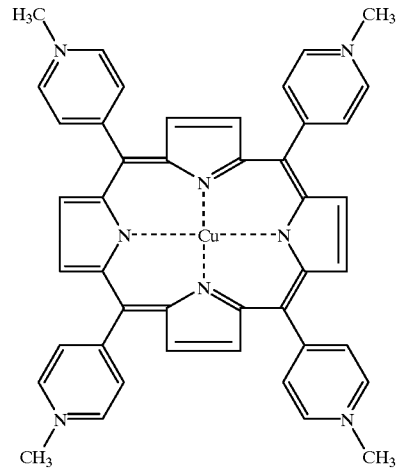

or the porphine is Co-meso-tetra-(4-sulfanatophenyl)-porphine or Co-meso-tetra-(N-methyl-4-pyridyl)-porphine, having the following structures, respectively:

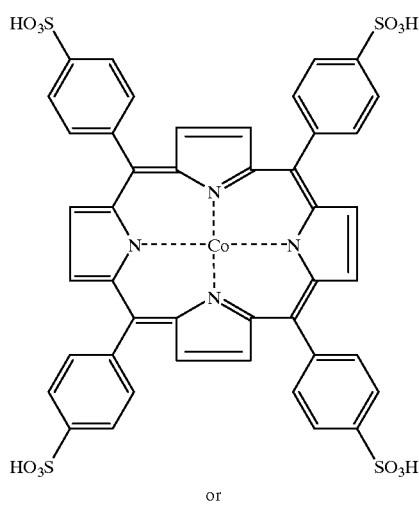

or

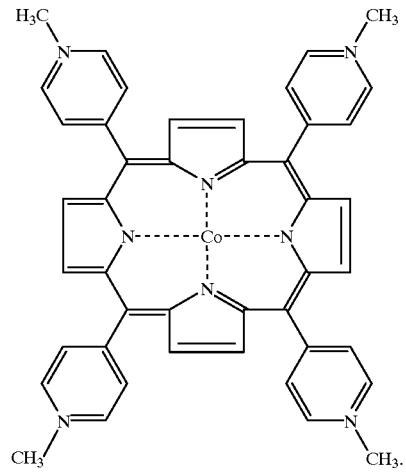

22. The composition of claim 21, further comprising a metal or a metal salt.

23. The composition of claim 22, wherein the metal or metal salt comprises a lanthanide or lanthanide salt.

24. The composition of claim 23, wherein the lanthanide or lanthanide salt comprises europium or europium salt.

25. The composition of claim 19, wherein the porphine is associated with a molecular includant.

26. The composition of claim 25, wherein the molecular includant is one or more cyclodextrins.

27. The composition of claim 26, wherein the one or more cyclodextrins comprise α-cyclodextrin, β-cyclodextrin, γ-cyclodextrin, δ-cyclodextrin, hydroxypropyl β-cyclodextrin, or hydroxyethyl β-cyclodextrin.

28. The composition of claim 19, wherein the colorant comprises a triarylmethyl dye, a monoazo dye, a thiazine dye, an oxazine dye, a naphthalimide dye, an azine dye, a cyanine dye, an indigo dye, a coumarin dye, a benzimidazole dye, a paraquinoidal dye, a fluorescein dye, a diazonium salt dye, an azoic diazo dye, a phenylenediamine dye, a diazo dye, an anthra-quinone dye, a trisazo dye, a xanthene dye, a proflavine dye, a sulfonaphthalein dye, a phthalocyanine dye, a carotenoid dye, a carminic acid dye, an azure dye, an acridine dye, or a combination thereof.

29. The composition of claim 22, wherein the composition further contains at least one metal solubility-enhancing agent.

30. The composition of claim 29, wherein the at least one metal solubility-enhancing agent comprises ethylenediaminetetraacetic acid or ethylene glycol-bis(β-aminoethyl ether).

31. The composition of claim 25, wherein the molecular includant comprises a clathrate or intercalate, a zeolite, a cyclodextrin, or a combination thereof.

32. The composition of claim 25, wherein the porphine is covalently bonded to the molecular includant.

33. The composition of claim 19, wherein the composition contains a solvent, wherein the solvent comprises an amide, a sulfoxide, a ketone, an aliphatic hydrocarbon, an aromatic hydrocarbon, an ester, water, or a combination thereof.

34. The composition of claim 19, wherein the composition contains a solvent, wherein the solvent comprises N,N-dimethylformamide; dimethylsulfoxide; acetone; methyl ethyl ketone; methyl butyl ketone; hexane; octane; benzene; toluene; xylene; ethyl acetate; water; or a combination thereof.

35. The composition of claim 25, wherein the composition contains a solvent, wherein the solvent comprises an amide, a sulfoxide, or water.

36. An ink set comprising two or more inks, wherein each ink of the ink set has a light fastness property, and at least two inks of the ink set have independent light fastness properties which are controlled and differ from one another; and wherein one or more inks of the ink set contain at least one colorant stabilizer, wherein the at least one colorant stabilizer comprises a porphine.

37. The ink set of claim 36, wherein the porphine is represented by the following formula

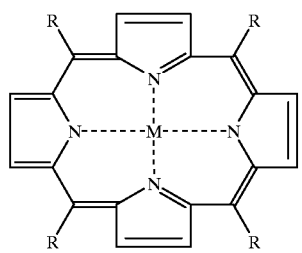

wherein M is iron, cobalt or copper; and wherein R is SO$_3$H,

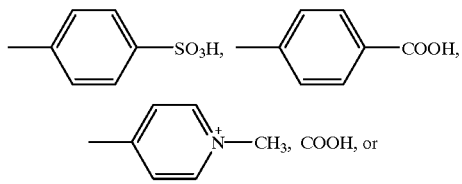

R$_1$COOH wherein R$_1$ is an alkyl group of from 1 to 6 carbons.

38. The ink set of claim 36, wherein the porphine is Cu-meso-tetra-(4-sulfanatophenyl)-porphine or Cu-meso-tetra-(N-methyl-4-pyridyl)-porphine, having the following structures, respectively:

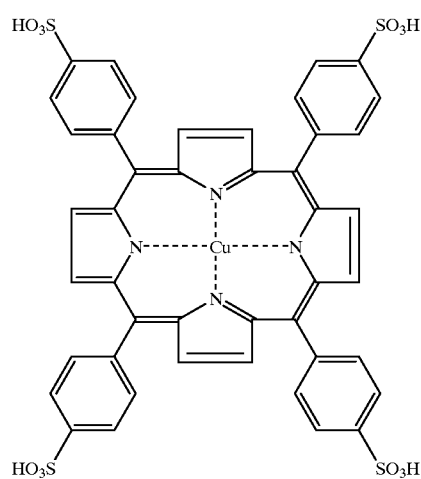

or

-continued

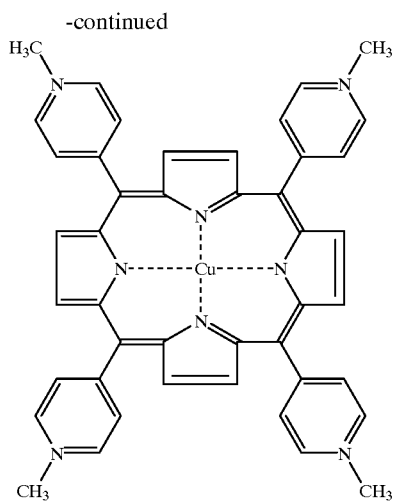

or the porphine is Co-meso-tetra-(4-sulfanatophenyl)-porphine or Co-meso-tetra-(N-methyl-4-pyridyl)-porphine, having the following structures, respectively:

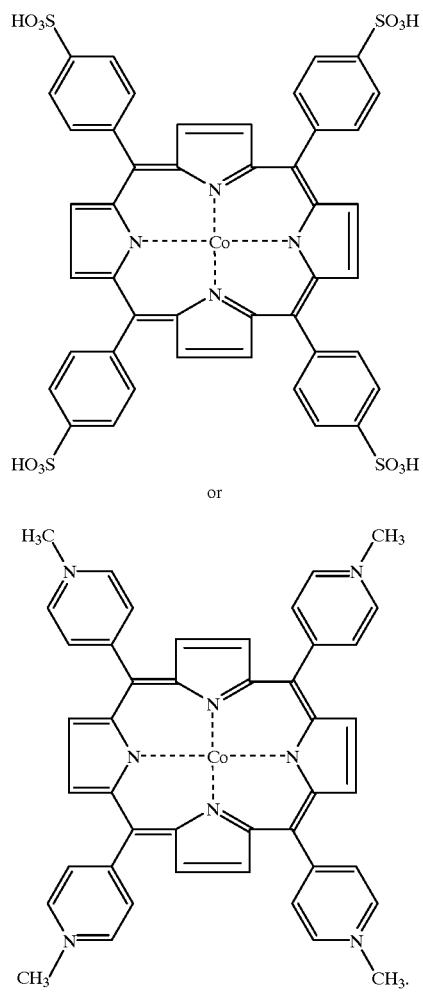

39. The ink set of claim 36, wherein a metal or metal salt is added to the one or more inks containing the porphine.

40. The ink set of claim 39, wherein the one or more inks containing the metal or metal salt further contains at least one metal solubility-enhancing agent.

41. The ink set of claim 40, wherein the at least one metal solubility-enhancing agent comprises ethylenediaminetetraacetic acid or ethylene glycol-bis(β-aminoethyl ether).

42. The ink set of claim 39, wherein the metal or metal salt comprises a lanthanide or lanthanide salt.

43. The ink set of claim 42, wherein the lanthanide or lanthanide salt comprises an europium or europium salt.

44. The ink set of claim 36, wherein the porphine is associated with a molecular includant.

45. The ink set of claim 44, wherein the molecular includant comprises a clathrate or intercalate, a zeolite, a cyclodextrin, or a combination thereof.

46. The ink set of claim 44, wherein the molecular includant is one or more cyclodextrins.

47. The ink set of claim 46, wherein the one or more cyclodextrins comprise α-cyclodextrin, β-cyclodextrin, γ-cyclodextrin, δ-cyclodextrin, hydroxypropyl β-cyclodextrin, or hydroxyethyl β-cyclodextrin.

48. The ink set of claim 44, wherein the porphine is covalently bonded to the molecular includant.

49. The ink set of claim 36, wherein one or more inks of the ink set contain a colorant, wherein the colorant comprises a triarylmethyl dye, a monoazo dye, a thiazine dye, an oxazine dye, a naphthalimide dye, an azine dye, a cyanine dye, an indigo dye, a coumarin dye, a benzimidazole dye, a paraquinoidal dye, a fluorescein dye, a diazonium salt dye, an azoic diazo dye, a phenylenediamine dye, a diazo dye, an anthra-quinone dye, a trisazo dye, a xanthene dye, a proflavine dye, a sulfonaphthalein dye, a phthalocyanine dye, a carotenoid dye, a carminic acid dye, an azure dye, an acridine dye, or a combination thereof.

50. The ink set of claim 36, wherein one or more inks of the ink set contain a solvent, wherein the solvent comprises an amide, a sulfoxide, a ketone, an aliphatic hydrocarbon, an aromatic hydrocarbon, an ester, water, or a combination thereof.

51. The ink set of claim 36, wherein one or more inks of the ink set contain a solvent, wherein the solvent comprises N,N-dimethylformamide; dimethylsulfoxide; acetone; methyl ethyl ketone; methyl butyl ketone; hexane; octane; benzene; toluene; xylene; ethyl acetate; water; or a combination thereof.

52. The ink set of claim 44, wherein the one or more inks containing the molecular includant further contains a solvent, wherein the solvent comprises an amide, a sulfoxide, or water.

53. The ink set of claim 36, wherein all inks of the ink set have independent light fastness properties which are controlled and differ from one another.

* * * * *